United States Patent [19]

Chance

[11] Patent Number: 5,792,051
[45] Date of Patent: *Aug. 11, 1998

[54] OPTICAL PROBE FOR NON-INVASIVE MONITORING OF NEURAL ACTIVITY

[75] Inventor: Britton Chance, Marathon, Fla.

[73] Assignee: Non-Invasive Technology, Inc., Philadelphia, Pa.

[*] Notice: The term of this patent shall not extend beyond the expiration date of Pat. No. 5,187,672.

[21] Appl. No.: 711,446

[22] Filed: Sep. 6, 1996

Related U.S. Application Data

[63] Continuation-in-part of Ser. No. 876,364, Apr. 30, 1992, abandoned, Ser. No. 320,160, Oct. 7, 1994, and Ser. No. 349,839, Dec. 2, 1994, said Ser. No. 876,364, is a continuation of Ser. No. 287,847, Dec. 21, 1988, Pat. No. 5,119,815, said Ser. No. 320,160, is a continuation of Ser. No. 900,197, Jun. 17, 1992, Pat. No. 5,353,799, which is a continuation-in-part of Ser. No. 644,090, Jan. 22, 1991, Pat. No. 5,187,672.

[51] Int. Cl.$^6$ .......................................... A61B 5/00
[52] U.S. Cl. ........................ 600/310; 600/473; 600/476
[58] Field of Search ................................ 128/633, 664, 128/665; 600/310, 311, 322, 340, 473, 476

[56] References Cited

U.S. PATENT DOCUMENTS

| | | |
|---|---|---|
| 4,281,645 | 8/1981 | Jöbsis . |
| 4,556,057 | 12/1985 | Hiruma et al. . |
| 4,675,529 | 6/1987 | Kushida . |
| 4,714,341 | 12/1987 | Hamaguri et al. . |
| 4,800,885 | 1/1989 | Johnson . |
| 4,824,242 | 4/1989 | Frick et al. . |
| 4,832,035 | 5/1989 | Cho et al. . |
| 4,836,207 | 6/1989 | Bursell et al. . |
| 4,846,183 | 7/1989 | Martin . |
| 4,908,762 | 3/1990 | Suzuki et al. . |
| 4,972,331 | 11/1990 | Chance .......................... 364/550 |
| 5,057,695 | 10/1991 | Hirao et al. .................... 250/575 |
| 5,062,431 | 11/1991 | Potter ............................ 128/665 |
| 5,119,815 | 6/1992 | Chance ......................... 128/633 |
| 5,187,672 | 2/1993 | Chance et al. ................ 364/550 |
| 5,190,039 | 3/1993 | Takeuchi et al. ............. 128/633 |
| 5,198,977 | 3/1993 | Salb ............................... 128/633 |

FOREIGN PATENT DOCUMENTS

WO 92/20273  11/1992  WIPO .

OTHER PUBLICATIONS

Bonner et al., "Model for photon migration in turbid biological media," *J. Opt. Soc. Am. A.*, 4(3):423–432, 1987.

Chance et al., "Comparison of Time–Resolved and Unresolved Measurements of Deoxyhemoglobin in Brain," *Proc. Natl. Acad. Sci. USA*, 85:4971–4975, 1988.

Delpy et al., "Estimation of optical pathlength through tissue from direct time of flight measurement," *Phys. Med. Biol.*, 33(12):1433–1442, 1988.

Jöbsis, "Noninvasive, Infrared Monitoring of Cerebral and Myocardial Oxygen Sufficiency and Circulatory Parameters," *Science*, 198:1264–1266, 1977.

(List continued on next page.)

*Primary Examiner*—Jennifer Bahr
*Assistant Examiner*—Eric F. Winakur
*Attorney, Agent, or Firm*—Fish & Richardson P.C.

[57] ABSTRACT

The invention features an optical probe for non-invasive monitoring of neural activity. The optical probe includes a light source constructed to introduce electromagnetic radiation of a visible or infra-red wavelength into biological tissue at an input port; and a detector constructed to detect, at a detection port, radiation of the selected wavelength that has migrated in the biological tissue from the input port. The optical probe also includes a processor, receiving signals of the detected radiation, constructed and arranged to determine neural activity of the tissue by measuring scattering or absorptive properties of the tissue. The neural activity detected by the optical probe includes redistribution of $K^+$, $Na^+$ and $H_2O$, which may occur upon death, during hypoxia, ischemia, or other physiological process.

38 Claims, 14 Drawing Sheets

OTHER PUBLICATIONS

Jöbsis–Vander Vliet, Non–Invasive, Near Infrared Monitoring of Cellular Oxygen Sufficiency In Vivo, *Oxygen Transport to Tissue VII*, pp. 833–841, 1986.

Lakowicz, "Gigahertz Frequency–Domain Fluorometry: Resolution of Complex Intensity Decays, Picosecond Processes and Future Developments," *Photon Migration in Tissues*, pp. 169–186, 1989.

Maris et al., "Frequency Domain Measurements of Changes of Optical Pathlength during Spreading Depression in a Rodent Brain Model," *SPIE, Time–Resolved Spectroscopy and Imaging of Tissues*, 1431;136–148, 1991.

Mayevsky et al., "A fiber optic based multiprobe system for intraoperative monitoring of brain functions," *SPIE, Time–Resolved Spectroscopy and Imaging of Tissues*, 1431:303–313, 1991.

Nioka et al., "The Relationship of Hemoglobin Oxygen Saturation and Energy Metabolism in Dog Brain," *Am. J. Physiol.*, 1989.

Sevick et al., "Quantitation of Time–and Frequency–Resolved Optical Spectra for the Determination of Tissue Oxygenation," *Analyt. Biochem.*, 195:330–351, 1991.

Tamura et al., "The Simultaneous Measurements of Tissue Oxygen Concentration and Energy State by Near–Infrared and Nuclear Resonance Spectroscopy," *Oxygen Transport to Tissue X*, pp. 359–363, 1988.

Tamura et al., "In Vivo Study of Tissue Oxygen Metabolism Using Optical and Nuclear Magnetic Resonance Spectroscopies," *Annu. Res. Physiol.*, 51:831–834, 1989.

Cat Head Hb 760/790 90°

Skull and Brain with Hemoglobin
90°, 760 and 790nm

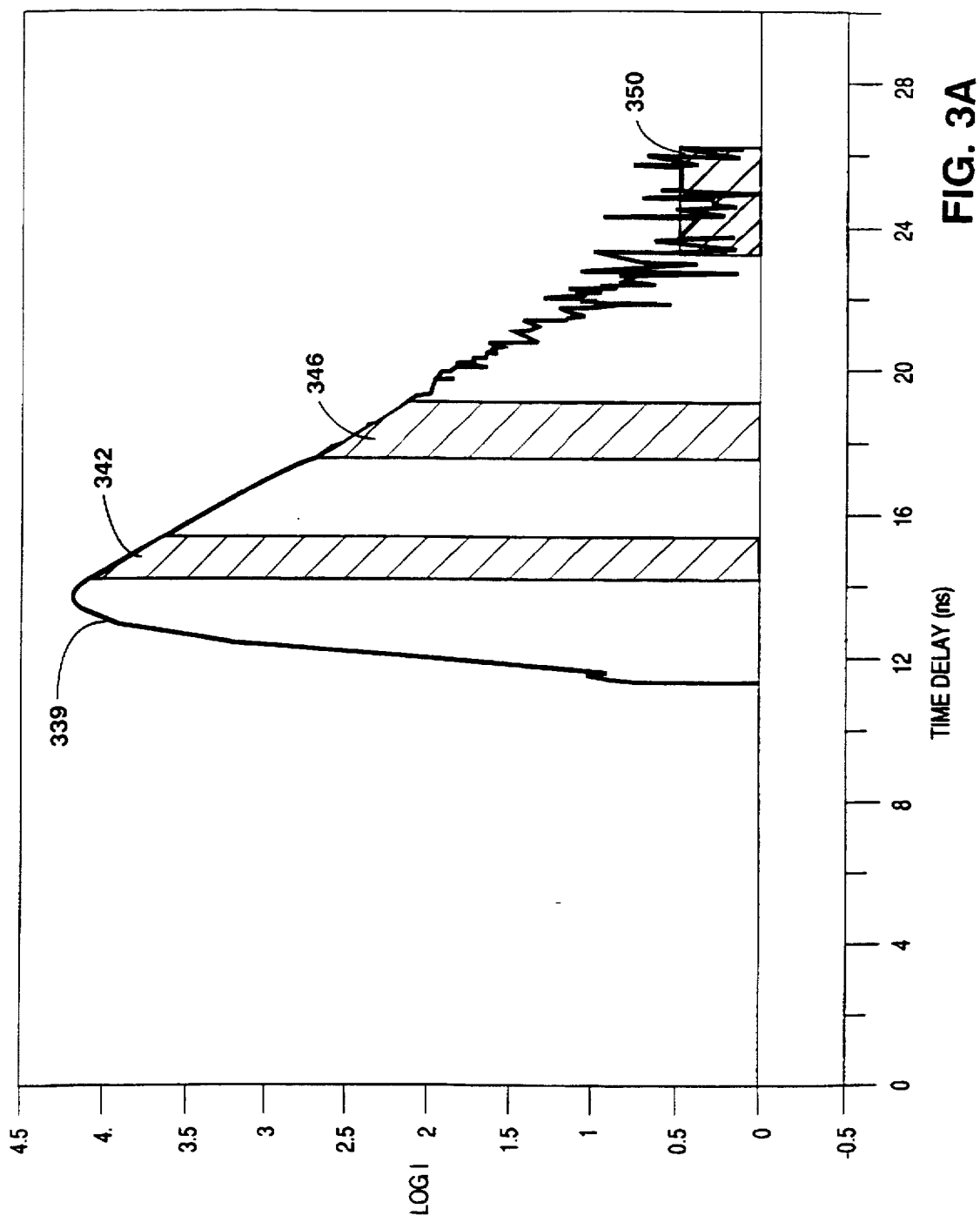

OPTICAL PROBE FOR NON-INVASIVE MONITORING OF NEURAL ACTIVITY

CROSS REFERENCE TO RELATED APPLICATIONS

The present application is a continuation-in-part of a U.S. patent application Ser. No. 07/876,364 filed Apr. 30, 1992, now abandoned, which is a continuation application of Ser. No. 287,847, filed Dec. 21, 1988, now U.S. Pat. No. 5,119,815, issued Jun. 9, 1992. The present application is also a continuation-in-part of a U.S. patent application Ser. No. 08/320,160 filed Oct. 7, 1994, which is a continuation application of U.S. Ser. No. 07/900,197 filed Jun. 17, 1992, now U.S. Pat. No. 5,353,799, which in turn is a continuation-in-part of a U.S. patent application Ser. No. 07/644,090 filed Jan. 22, 1991, now U.S. Pat. No. 5,187,672. The present application is also a continuation-in-part of a U.S. patent application Ser. No. 08/349,839, filed Dec. 2, 1994. The above-referenced applications are incorporated by reference as if fully set forth in their entireties herein.

BACKGROUND OF THE INVENTION

The present invention relates to different optical probes for non-invasive in vivo measurement of neural activity of different types of biological tissues.

Time resolved spectroscopy, phase modulation spectroscopy, and continuous wave spectroscopy have been used as a useful non-invasive tool to measure and monitor tissue oxygenation by employing light of visible and infrared wavelenghts sensitive to oxy- and deoxy-hemoglobin. Various different apparatuses that employ the above-mentioned spectroscopies have been described.

SUMMARY OF THE INVENTION

The present invention provides an optical probe and a method for detecting a pathophysiological change in biological tissue of a subject. The pathophysiological change is related to neural activity of the examined tissue. The invention may also monitor hemoglobin deoxygenation and/or oxygenation in the subject, and correlate the hemoglobin deoxygenation and/or oxygenation to an intracellular event. The intracellular event may include a reduction of $NAD^+$, release of $K^+$ from cells, shift of extracellular Na, Ca or other solutes into the cells, or a loss of electrical activity. The invention is particularly useful for detecting and/or early warning of neural damage.

The invention features an optical probe for non-invasive monitoring of neural activity. The optical probe includes a light source constructed to introduce electromagnetic radiation of a visible or infra-red wavelength into biological tissue at an input port; and a detector constructed to detect, at a detection port, radiation of the selected wavelength that has migrated in the biological tissue from the input port. The optical probe also includes a processor, receiving signals of the detected radiation, constructed and arranged to determine neural activity of the tissue by measuring scattering or absorptive properties of the tissue.

In one aspect, the optical probe may further include a first oscillator constructed to generate a first carrier waveform at a first frequency on the order of $10^8$ Hz, the first frequency having a time characteristic compatible with the time delay of photon migration from the input port to the detection port in the examined tissue. The light source is coupled to the first oscillator and constructed to generate the radiation modulated by the first carrier waveform. The optical probe further includes a phase detector constructed to determine change in waveform of the detected radiation relative to the waveform of the introduced radiation and determine therefrom the phase shift of the detected radiation at the wavelength, the phase-shifted radiation being indicative of the scattering and absorptive properties of the examined tissue. The processor determines the neural activity based on the phase shift.

The optical probe may further include a second oscillator constructed to generate a second waveform at a second frequency. The detector arranged to receive a reference waveform at a reference frequency offset by a frequency on the order of $10^3$ Hz from the first frequency and to produce a signal, at the offset frequency, corresponding to the detected radiation. The phase detector adapted to compare, at the offset frequency, the detected radiation with the introduced radiation and to determine therefrom the phase shift at the wavelength.

The processor may be constructed and arranged to calculate the effective pathlength of photons of the wavelength migrating between the input port and the detection port prior to determining the neural activity. The processor may be constructed and arranged to calculate, at the employed wavelength, the scattering coefficient, or the absorption coefficient, of the examined tissue prior to determining the neural activity.

The optical probe may include a light source, operatively connected to the first oscillator, constructed to generate electromagnetic radiation of a second selected wavelength modulated by the first carrier waveform. The optical probe further includes a switch adapted to introduce interchangeably radiation at each of the wavelengths into the light guide. The detector is adapted to detect, at the detection port, the radiation of the second wavelength that has migrated in the tissue between the input and detection ports. The phase detector, operatively connected to the switch, is adapted to compare, at each of the wavelengths, the detected radiation with the introduced radiation and to determine therefrom the phase shift of the detected radiation. The processor determines the neural activity based on the phase shift.

The processor may be constructed and arranged to calculate the effective pathlength of photons of the second wavelength migrating between the input port and the detection port prior to determining the neural activity.

The processor may be constructed and arranged to calculate, at the second wavelength, the scattering coefficient, or the absorption coefficient, of the examined tissue prior to determining the neural activity.

In another aspect, the optical probe includes a light source is constructed to generate pulses of radiation of the wavelength, the pulses having duration on the order of a nanosecond or less. The detector is constructed to detect over time photons of modified pulses that have migrated in the tissue from the input port. The probe further includes an analyzer, connected to the detector, adapted to determine a change in the pulse waveform shape of the detected pulses relative to the introduced pulses, at the wavelength, and a processor determining the neural activity based on the determined pulse waveform change.

The processor may be constructed and arranged to calculate the effective pathlength of photons of the wavelength migrating between the input port and the detection port prior to determining the neural activity.

The processor may be constructed and arranged to calculate, at the wavelength, the scattering coefficient, or the absorption coefficient of the examined tissue prior to determining the neural activity.

The optical probe may include a light source further adapted to introduce into the tissue, at the input port, the pulses of electromagnetic radiation of a second selected wavelength in the visible or infra-red range. The detector is further adapted to detect, at the detection port, photons of modified pulses of the second wavelength that have migrated in the tissue from the input port. The analyzer further constructed to determine a change in the pulse waveform shape of the detected pulses relative to the introduced pulses, at the second wavelength, and the processor is further adapted to determine the neural activity based on the determined pulse waveform change at each the selected wavelength.

The processor may be constructed and arranged to calculate the effective pathlength of photons of the second wavelength migrating between the input port and the detection port prior to determining the neural activity.

The processor may be constructed and arranged to calculate, at the second wavelength, the scattering coefficient, or the absorption coefficient of the examined tissue prior to determining the neural activity.

The neural activity detected by the optical probe includes redistribution of $K^+$, $Na^+$ and $H_2O$; these may occur upon death, during hypoxia, ischemia or other physiological processes described below.

BRIEF DESCRIPTION OF THE DRAWING

FIG. 3A and 3B show a typical time resolved spectrum and a timing diagram for the system of FIG. 3, respectively.

DESCRIPTION OF THE PREFERRED EMBODIMENT

Figure 1:
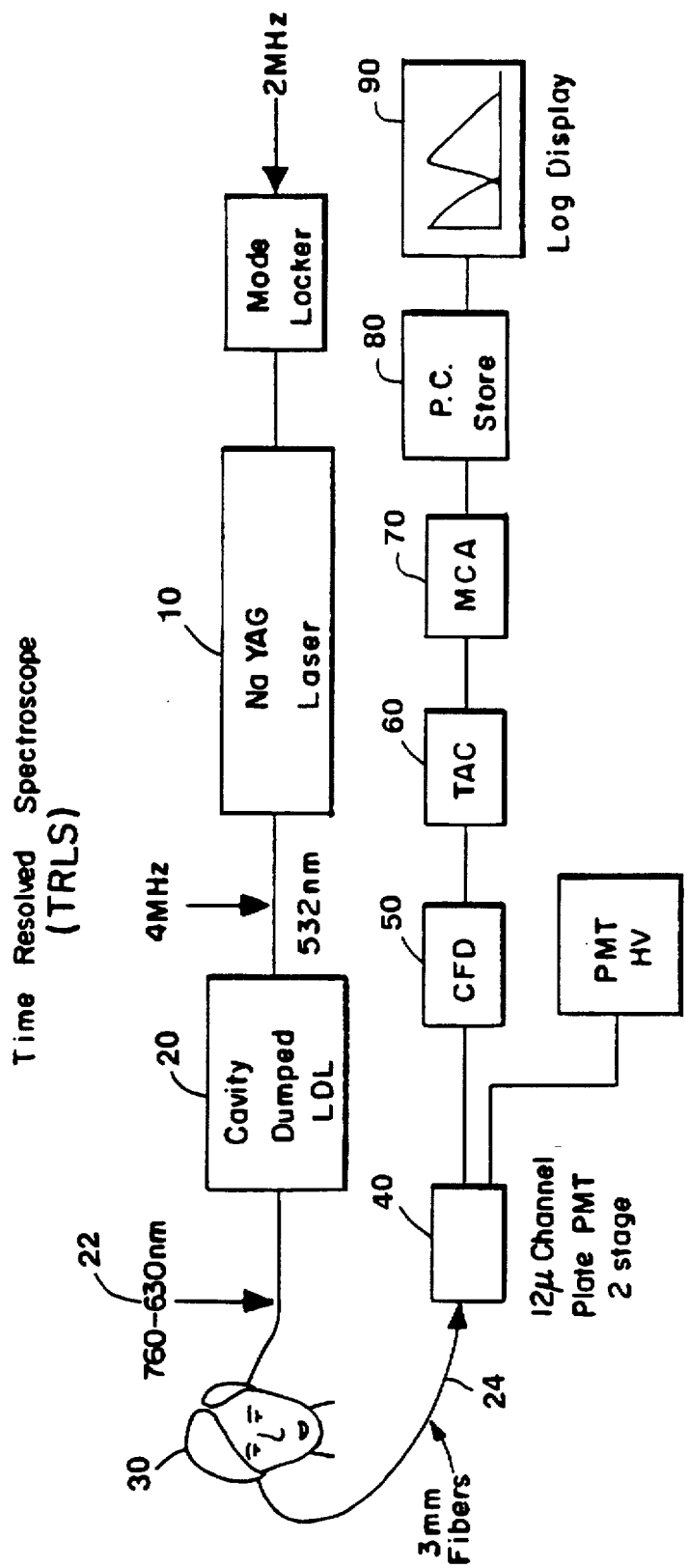
FIG. 1 is a block diagram of a time resolved probe used for monitoring of the brain tissue.

Referring to FIG. 1, as described in the U.S. Pat. 5,119, 815, a 2 MHz signal is input to a mode-locking circuit to achieve short pulse widths. The signal from the mode locking circuit is in turn connected to a cavity dumped neodymium yttrium-aluminum-garnet (YAG) laser 10 to determine the pulse characteristics. The cavity dumped neodymium YAG laser 10 is used to excite a liquid dye laser 20 and generate short light pulses by cavity dumping. A 4 MHz signal is injected into the output pulse of the YAG laser 10 prior to its introduction into the liquid dye laser 20. Thus, in a preferred embodiment, the YAG laser 10 acts as a mode-locked exciter which is frequency doubled to 532 nm and excites a flowing stream of Syril dye (LDF 751, Exciton, Inc.) resulting in the activation of the liquid dye laser and producing a pulse having a wavelength of 760 nm with a repetition rate of 4 MHz. Depending upon the desired output frequency, the liquid dye laser also may preferably contain dyes ranging from styryl (760 nm) to Rhodamine 6G (630 nm). In a most preferred embodiment, a pulse train about 6 picoseconds ($6 \times 10^{-12}$ sec) in duration, and of an average intensity of about 30 milliwatts (mW) is generated. This embodiment may also use other lasers generating light in the visible to infra-red range of wavelenghts.

The light pulses are coupled to the subject 30 via input light guide 22 and output light guide 24. In FIG. 1, the light guides 22, 24 are shown affixed to the head of a subject 30. The light guides 22, 24 are flexible fiber optic guides, about 3 millimeters (mm) in diameter. It has been found through experimentation that exiting photons can be accumulated from points 2–10 centimeters (cm) apart on the circumference of the head, particularly the forehead. Therefore, when used on the forehead of a subject, a shown in FIG. 1, the distance between the input light guide 22 and the output light guide 24 should be between about 2 to 10 cm.

A detector 26 is connected to the output light guide 24. Preferably, the detector employed is a micro-channel plate detector. The detector 26 is in turn connected to a photo-multiplier 40, for intensifying the signal. As will be understood by those of ordinary skill, the micro-channel plate detector 26 will have adequate gain, and preferably has time resolution on the order of about 50 picoseconds. Since the rise and fall times of the observed light pulse occur between 1.5 and 3.5 nanoseconds (ns) following the input pulse, in a preferred embodiment a 12 micro-channel plate, two-stage photomultiplier (e.g., Hamamatsu) provides an appropriate time resolution of approximately 100 picoseconds (0.1 ns), as required for these studies. A photomultiplier tube high voltage source 70 is also connected to the photo-multiplier 40.

The output of the photomultiplier 40 is connected to a photon counting system in which roughly 100 "time bins"

are employed, to accumulate the number of photons received over a period of between about 30 to 60 seconds. While in this mode of operation, only a single photon can be accepted per bin at any given time, thus total count rates of up to 40,000 per second are feasible without significant loss due to "pile up" or overburdening of the queue waiting to be received. The time course of the input/output pulse amplitude is thereby obtained. The output of the photomultiplier 40 is then fed to a photon counting system, preferably comprised of a constant fraction discriminator 50, which is a pulse amplitude discriminator in which the threshold for acceptance of a pulse is a constant fraction of the peak amplitude of the pulse. The signal is next input to a time to amplitude converter or scintillation counter 60, which produces an output pulse whose amplitude is proportional to the time difference between start and stop pulses. A multichannel analyzer 70 and a personal computer 80 perform the final processing to convert the signal into a display format 90 or other data set.

In the presence of light absorptive materials, including biological tissue, tissue pigments such as hemoglobin and myoglobin, the decaying portion of the detected output is dominated at relatively long times by an exponential form:

$$I(t) = I_o \exp(-2.303 \, kt) \quad (1)$$

which is another expression of the generalized Beer-Lambert Law:

$$I(t) = I_o \exp(-2.303 \, R[C]L) \quad (2)$$

or more simply:

$$u = \frac{1}{L} \log \frac{I_o}{I} = EC \quad (I)$$

where E is the extinction coefficient, C is the concentration of the absorber, u is the specific absorption per unit length and L is the path length. The path length is simply related to t, the time required for light to traverse a given length, i.e., the "time of flight", by the equation:

$$L = ct/n \quad (4)$$

where c is the velocity of light in the medium of interest and n is the medium's average refractive index. For example, for water these values are about n=1.33 and c=23 cm/ns.

In a semi-logarithmic plot of the detected light intensity, an appropriately straight line with a negative slope is obtained. Since:

$$\log \frac{I_o}{I} = ECL = EC \frac{ct}{n}$$

This slope, u, is defined as:

$$u = \frac{1}{L} \log \frac{I_n}{I} = \frac{n}{ct} \log \frac{I_o}{I} = EC \quad (5)$$

In order to observe changes of absorption, for example, due to deoxygenation of oxyhemoglobin (HbO$_2$), then the concentration of the absorber may be calculated from the change in slope u:

$$\Delta C = \frac{\Delta u}{\Delta E} \quad (6)$$

From the Beer-lambert Law, an expression relating the optical density (OD) of the light to the concentration of the absorber may be derived:

$$OD = \log \frac{I_o}{I} = E[C]L \quad (7)$$

And accordingly, from equation (6), the concentration of an absorptive pigment, C, may be calculated:

$$\Delta C = \frac{\Delta_u}{\Delta E} \quad (9)$$

Thus, it is possible to determine the path length the photons travel by measuring changes in optical density and changes in absorptive and scattering properties of the measured tissue.

Figure 1A:
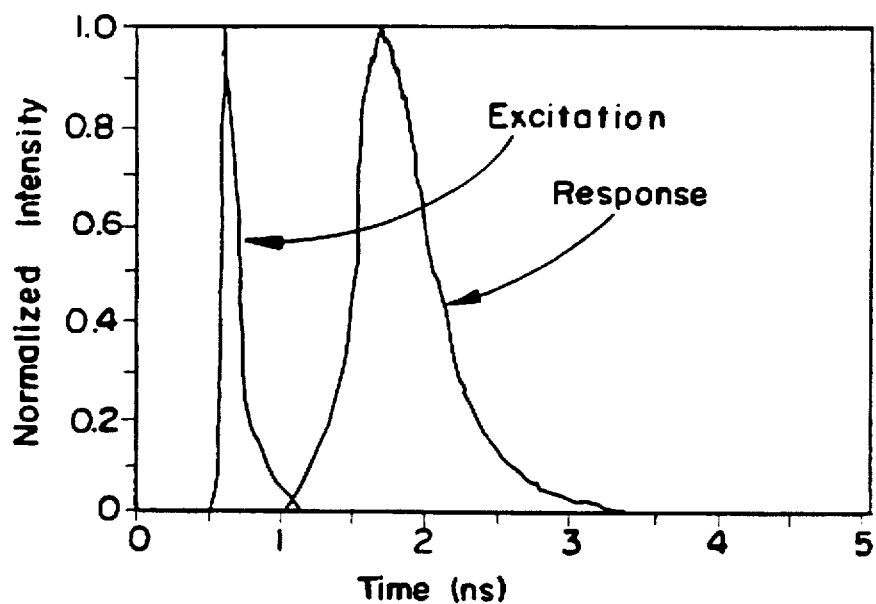
FIG. 1A depicts a plot of data describing intensity vs. time for light pulses collected from a human brain using the methods and apparatus of the present invention.
Figure 1B:
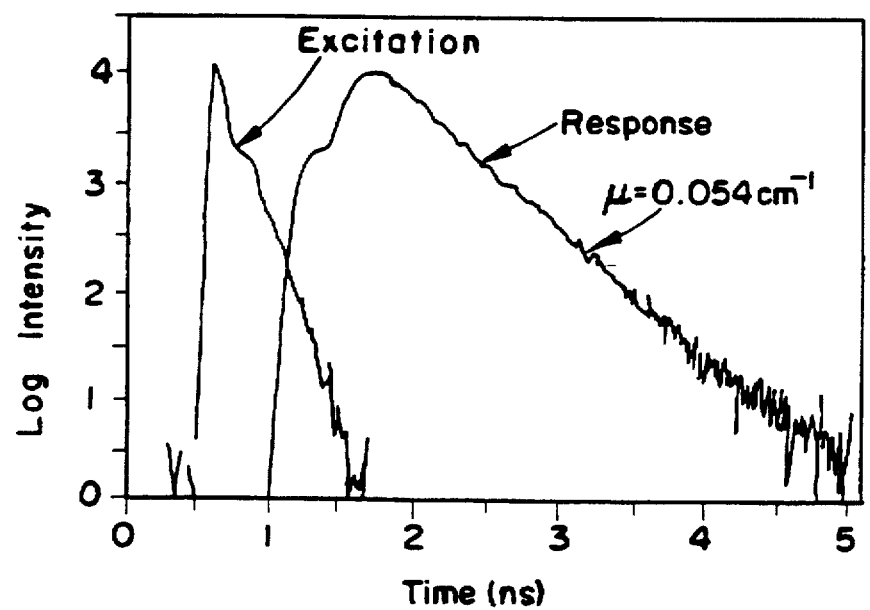
FIG. 1B depicts a plot of data describing intensity vs. time of light pulses collected from a human brain with the intensity data scaled logarithmically.
Figure 1C:
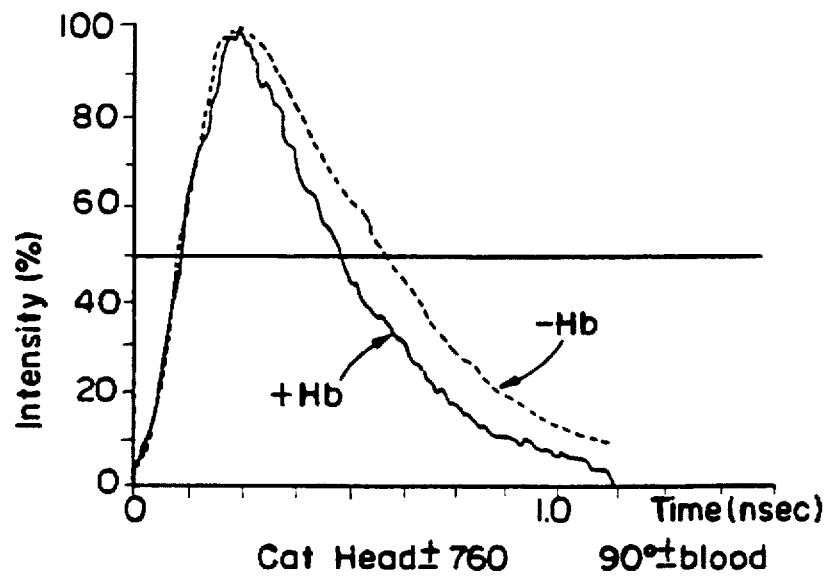
FIG. 1C represents a plot of intensity vs. time of light pulses in a cat brain before and after an infusion of hemoglobin.
Figure 2:
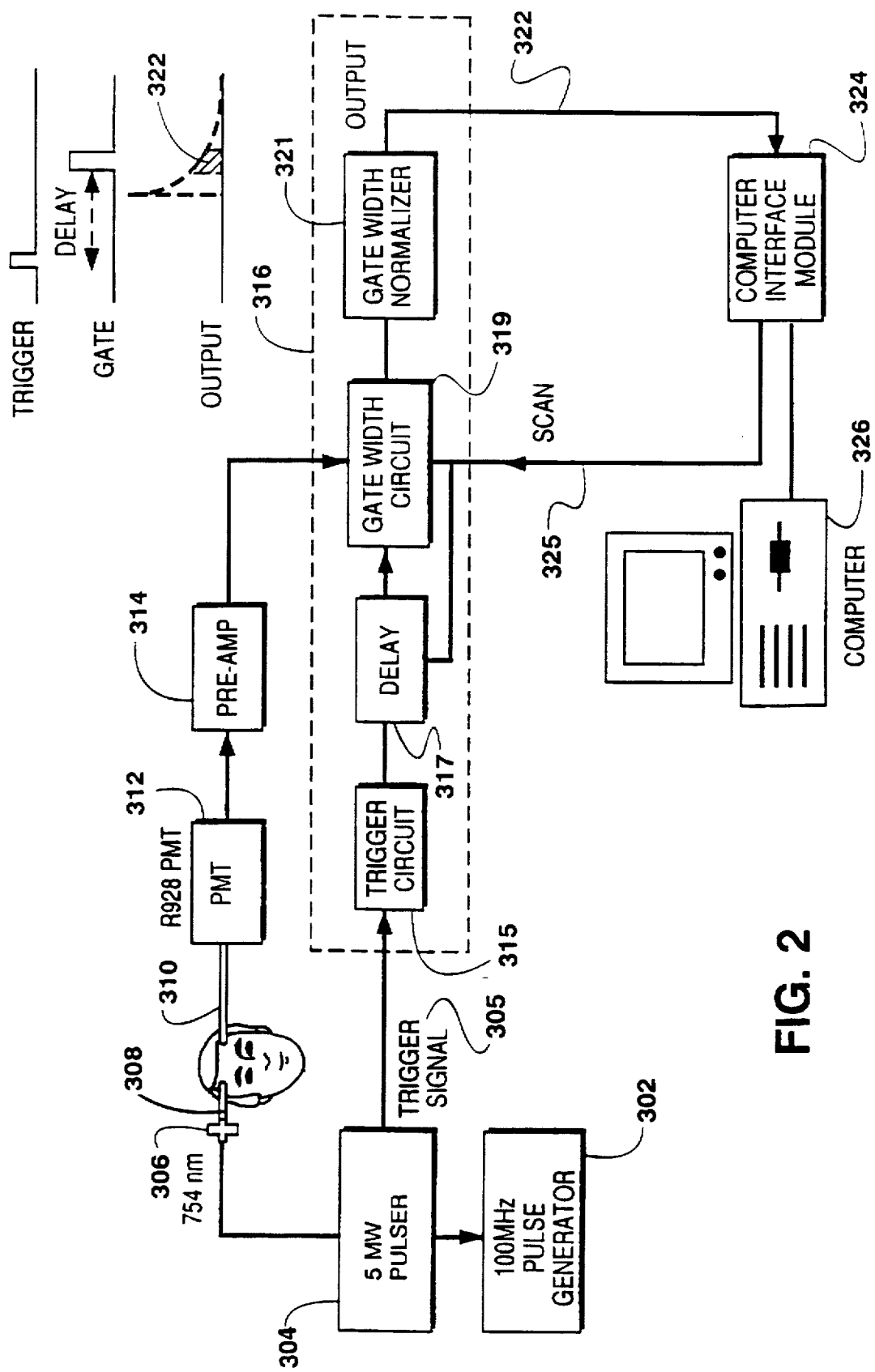
FIG. 2 is a block diagram of an TRS pulse system in accordance with another embodiment of the present invention.
Figure 3:
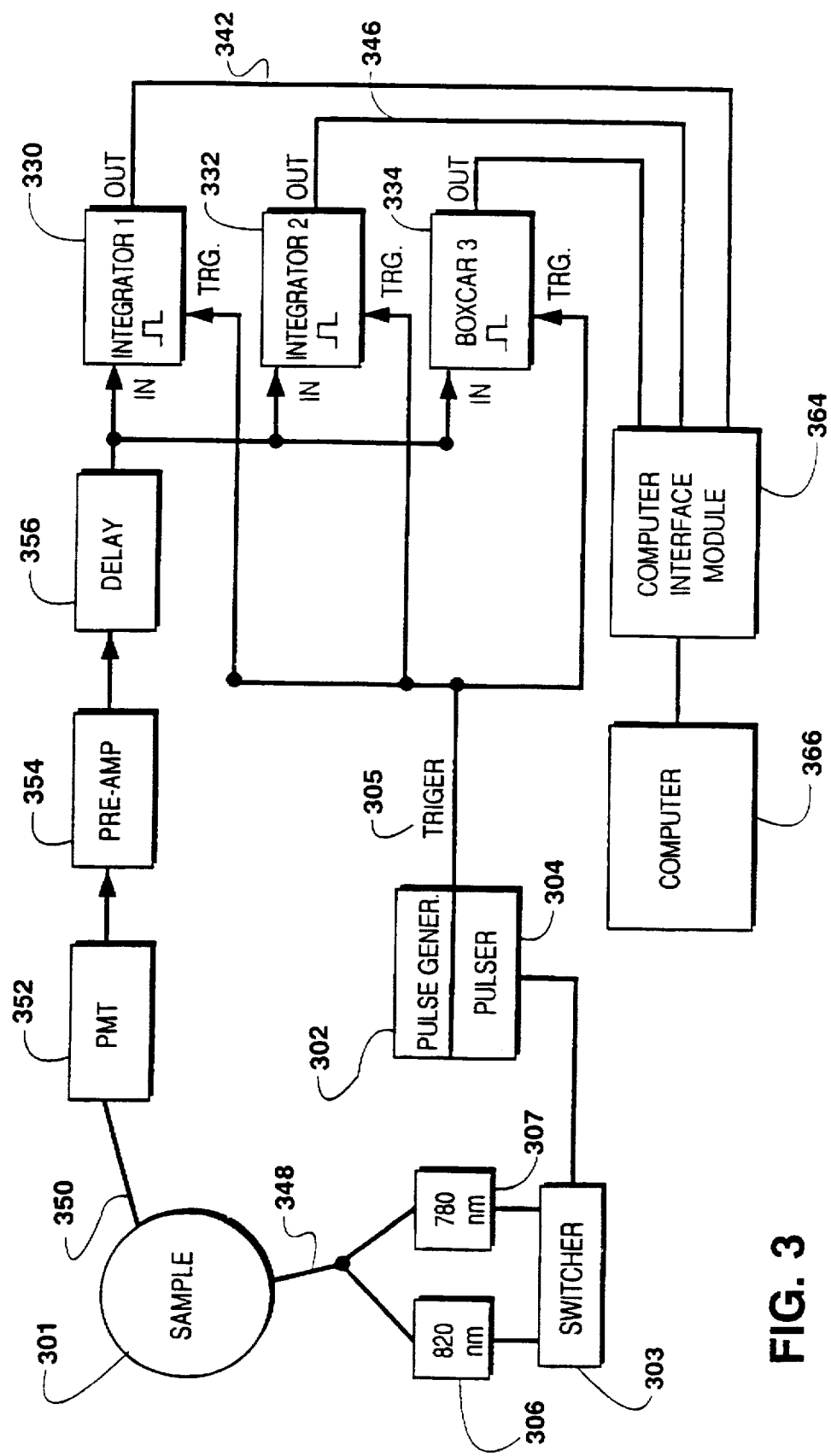
FIG. 3 is a block diagram of a multiple gate integrator TRS pulse system in accordance with another embodiment of the present invention.

The performance of the apparatus described above is shown in FIGS. 1A and 1B. These results are taken from a human brain. The display of the waveform of the initial pulse excitation, as shown in FIG. 2, is obtained by coupling the fibers together through a $10^{-4}$ (40 dB) attenuator; the waveform of the response is plotted on an amplitude vs. time on a linear scale. In FIG. 3, the same data are shown, however, the absorption data are now plotted on a logarithmic scale ($\log_{10}$). These results indicate that:

$$\mu = 1/L \log I_o/I$$

is constant for the larger part of the decay intensity of the exiting photons, i.e., between about 2–5 ns.

Figure 1D:
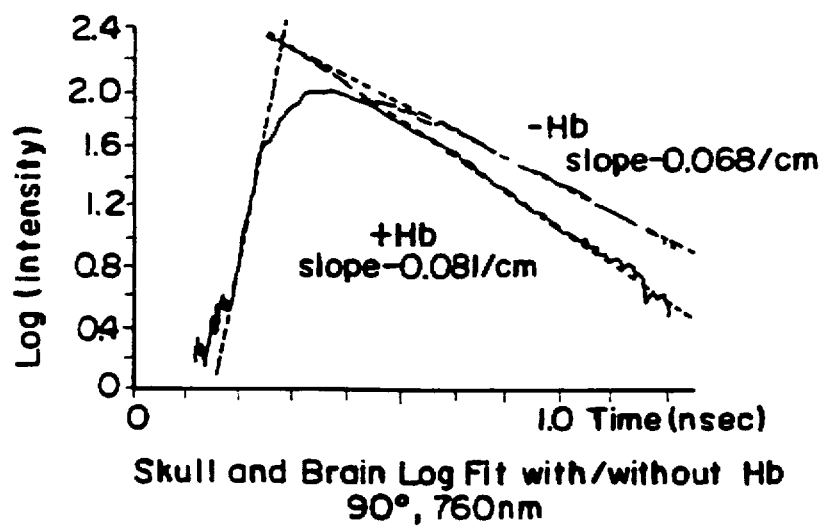
FIG. 1D represents a plot of intensity vs. time as shown in FIG. 1C with the intensity data scaled logarithmically.
Figure 1E:
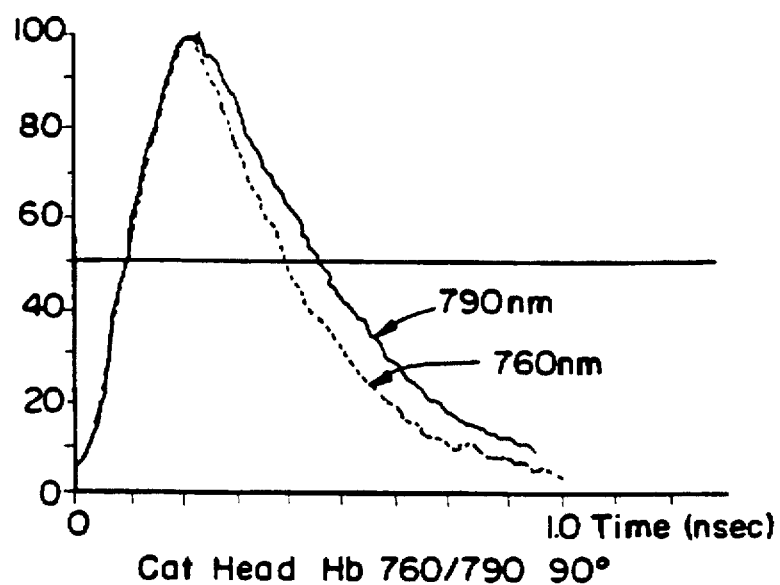
FIG. 1E represents a plot of intensity vs. time for a cat brain illustrating the effect of wavelength on decay kinetics.
Figure 1F:
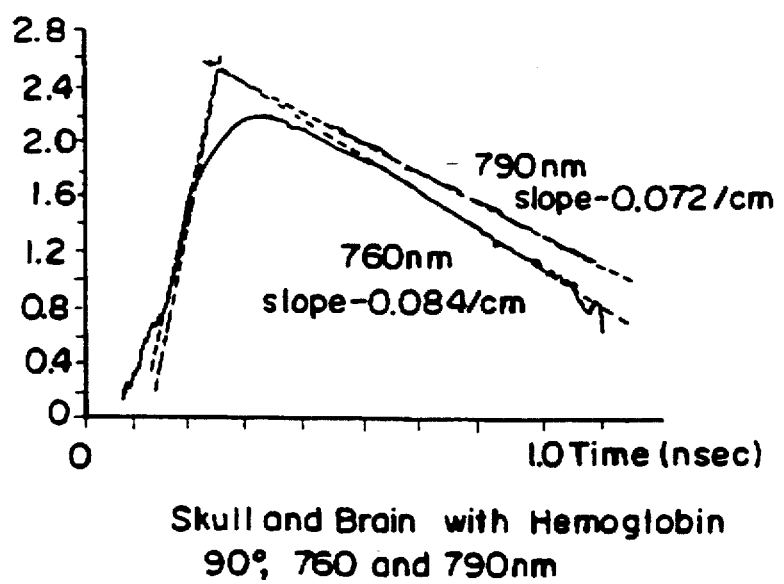
FIG. 1F represents a plot of intensity vs. time as shown in FIG. 1E with the intensity scaled logarithmically.

FIGS. 1C–1F depict the results of data taken from a preserved cat brain which has had hemoglobin injected into the contralateral hemisphere. FIG. 1E and FIG. 1F illustrate that an increment of absorption is much greater in the injected cat head when a wavelength of about 760 nm is used instead of about 790 nm, the absorption being much greater at the former wavelength.

To measure penetration depths in the brain, the time resolution of the photon migration within various tissues and the models was evaluated. The absorption of visible and NIR light in highly scattering material has been described in the literature. The duration of a short pulse of radiation introduced into a highly scattering object, such as the brain, is observed to be greatly prolonged because of the long path of photon migration to the receiver site. When there is a specific absorber such as Hb (measured at 760 nm), the number of photons detected will be appropriately diminished.

Two synchronously pumped, tunable dye lasers (Coherent Laser Products Division), operating at 760 and 790 nm and pumped by the second harmonic of a CW NdYAG (neodymium/yttrium/aluminum-garnet) mode-locked laser, were used as the light source. The pulse length was about six picoseconds (6.0 ps), the pulse energy was 1.3 nJ per pulse, and the average power was 100 mW at 77 MHz. The decay of the radiation was recorded with a 0.2-cm fiber-optic probe coupled to a streak camera (Hamamatsu). The fibers were placed at various positions with respect to the input light to record the migration of light to the exit fiber. The velocity of light, c/n, in the brain tissue is taken to be 0.023 cm/ps for a refractive index of 1.3. The signal-to-noise ratio was adequate for 3 decades of logarithmic plot. The time-difference determinations are accurate to 10 ps.

Figure 1G:
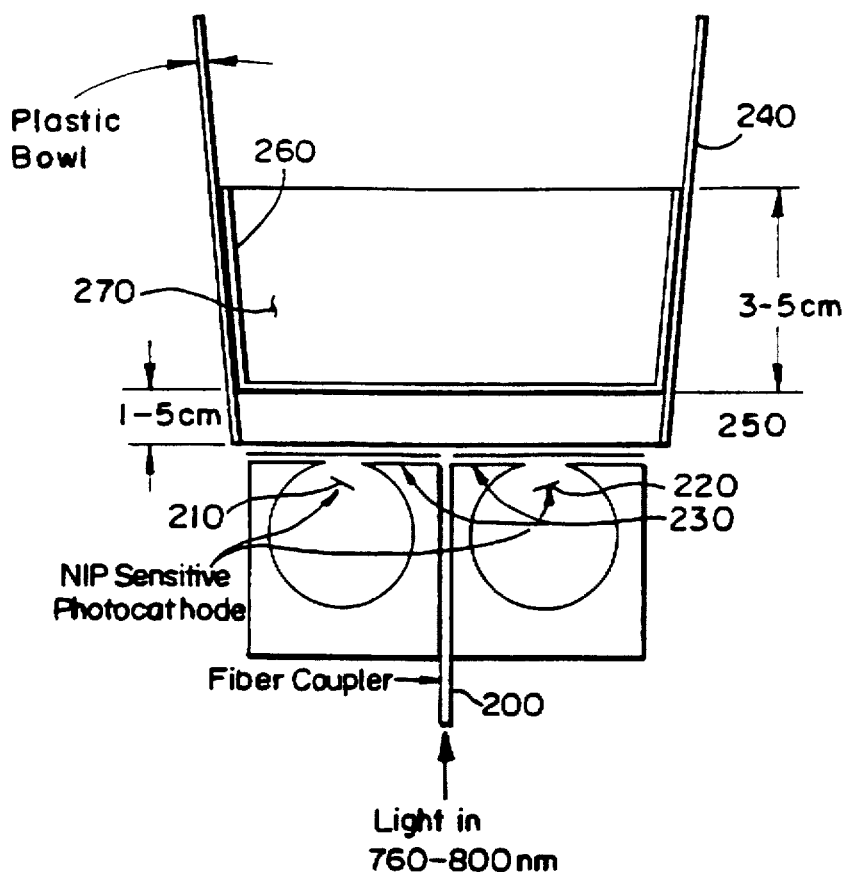
FIG. 1G is a partially schematic depiction of a continuous light spectrophotometer.
Figure 1H:
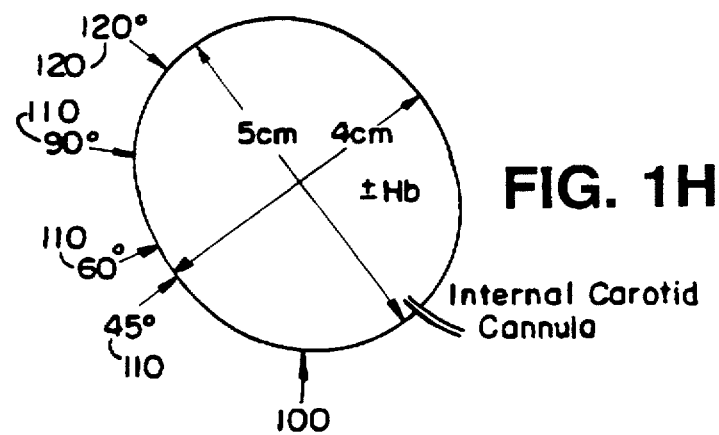
FIG. 1H is a schematic of a cat's head, showing the relative angels at which excitation and detection ports are located.

The geometry of the cat-head model used in this Example is illustrated in FIG. 1H, which indicates the point of input 100 of the laser light and the points 110, 120, at which a 0.2 cm diameter fiber probe was attached to obtain output signals. The points 110, 120 were chosen to correspond to the 2.0 cm separation of the milk model illustrated in FIG. 1G and three additional 3.0, 5.0, and 6.5 cm points at angles of 45 degrees, 60 degrees, and 90 degrees and 110 degrees, respectively.

To evaluate the changes of photon migration that occur when a known concentration (0.15 Mm) of Hb is added to a localized region of the brain, the model used met the following requirements: (i) the brain was initially hemoglobin free, (ii) there was a portion of brain into which Hb could be injected and in which Hb would be stable, (iii) the brain could be observed without or with the skull, and (iv) it could be transported readily. This model involves redistribution of $K^+$, $Na^+$, and $H_2O$ that occur on death. However, the values of the logarithmic slope do not differ greatly from the in vivo condition; 0.08 as compared to 0.07 $cm^1$.

The animal was anesthetized with ketamine and heparinized (400 units/kg of body weight). The head cleared of blood by exchange transfusion with Ringer's solution, which was followed by 10% (vol/vol) glycerol. Experimental observations were made before and after perfusion of one hemisphere (via the cannulated carotid artery) with Hb in blood cells at a normal hematocrit (40%). Subsequent analysis of the distribution of the hemoglobin showed 0.035 mM and 0.063 mM in the two hemispheres after reperfusion with blood.

FIGS. 1D and 1E show data obtained from a cat head before and after Hb injection at an angle of 90 degrees, which corresponds to a 4.2-cm distance between light input and output. In the absence of Hb, the half-width or scattering-time constant was 450 ps. When Hb was added to the contralateral hemisphere, a value of 360 ps was obtained. Referring to FIG. 5, the values of the logarithmic slope are 0.068 cm-1 and 0.081 cm-1, and $L_{1/2}$ values were 6.7 and 4.8 cm, respectively.

FIGS. 1E and 1F, the effect of wavelength upon the decay kinetics was measured at 760 and 790 nm. The angle between incidence and recording was 90 degrees. The specificity of wavelength dependence is shown; it is observed that the waveform decays more rapidly with 760-nm light than with 790-nm light. The scattering time constant at 790 nm is 430 ps, which decreases to 350 ps at 760 nm. Referring to FIG. 7, the logarithmic slope values are 0.072 and 0.084 cm-1, and the $L_{1/2}$ values are 5.8 and 4.2 cm, respectively.

Another preferred embodiment of the optical probe is described in the U.S. Pat. No. 5,386,827, which is incorporated by reference as if fully set forth herein. FIG. 2 shows diagrammatically implementation of the "boxcar" simplified TRS system that uses a single integrator for the gated photon signal integration. A pulse generator 302 operating at a frequency on the order of 100 MHz connected to a pulser 306 drives a laser 306 (e.g., Hamamatsu PLP-10 pulsed laser diode). Laser 306 generates a train of light pulses of a selected wavelength (e.g., 754 nm) and constant duration on the order of 100 psec (Pulses of the order of a nanosecond can also be used). The light pulses are coupled to an optical fiber 308 and are introduced to subject 300 at an input port. Transmitted photons migrate in the subject and arrive at a detection port of an optical fiber 310. In the migration process, the input pulse has been modified by the scattering and absorptive properties of tissue of subject 300. Photons arriving at the detection port are transmitted to a detector 312, (for example, Hamamatsu photomultipliers R928, R1517, MCP R1712, R1892 or other).

The output of detector 312 is amplified in a wide band preamplifier/impedance changer 314 and coupled to a boxcar integrator 316. Integrator 316 activated by a pulse gate collects all arriving photons over a predetermined time interval. The integrator output (322) is sent to computer interface module 324. Computer 326 stores the total number of counts detected during the collection interval of integrator 316.

Integrator 316 includes a trigger 315 that is triggered by a signal 305 from pulser 304. Trigger 315 activates a delay gate 317 that, in turn, starts counting of all detected photons during the time interval specified by a gate width 319. Output from a gate width normalizer 321 is an analog signal or a digital signal representing all photons that arrived at the detection port during the preselected gate width interval. A suitable integrator can be achieved by using SR 250 manufactured by Stanford Research Systems.

Depending on the application, computer 326 sets the delay time of delay gate 317 and the gate width time of gate width circuit 319. The system can scan integration gate widths over the whole time profile of the detected pulse. Gate width normalizer 321 adjusts the width of the integration time depending on the detected signal level. The gate width may be increased logarithmically for smaller signals in accordance with the exponential decay of the fall of the detected pulse; this increases the signal to noise ratio. The system operates at a repetition rate of at least 10 KHz.

Referring to FIG. 3, alternatively, multiple (at least three), parallel integrators are used in a faster and more efficient system. This system, same as the system of FIG. 2, may be used to determine the whole profile of the detected pulse (339) shown in FIG. 3A, by appropriately selecting the delay gates and the gate widths.

Pulse generator 302 connected to a pulser 304 drive alternately laser 306 and 307. The alternate coupling is provided by a switcher 303 that operates at frequencies on the order of $10^7$ Hz. Pulses of light of wavelength in the visible or infra-red range and duration $10^{-9}$ to $10^{-10}$ second are alternately coupled to subject 10 via optical fibers 348 or other light guide. The light pulses are modified by tissue of subject 301 positioned between the input port of fiber 348 and the detection port of fiber 354. The modified pulses are detected by detector 352 and the detected signal is amplified by preamplifier 354. Integrators 330, 332 and 334 collect data during selected gate width intervals, as shown on the timing diagram of FIG. 3B. Trigger 305 correlated with the input pulse, triggers delay gates 1, 2, and 3 (shown in FIG. 3B) that are set to have selected delay times. Each delay gate then triggers its corresponding integrator that collects all photons that arrive at the detector during the delay width time. Each integrator collects photons arriving at the detection port during its integration time defined by the gate width. This configuration can achieve a repetition rate of at least 10 kHz.

Figure 3B:
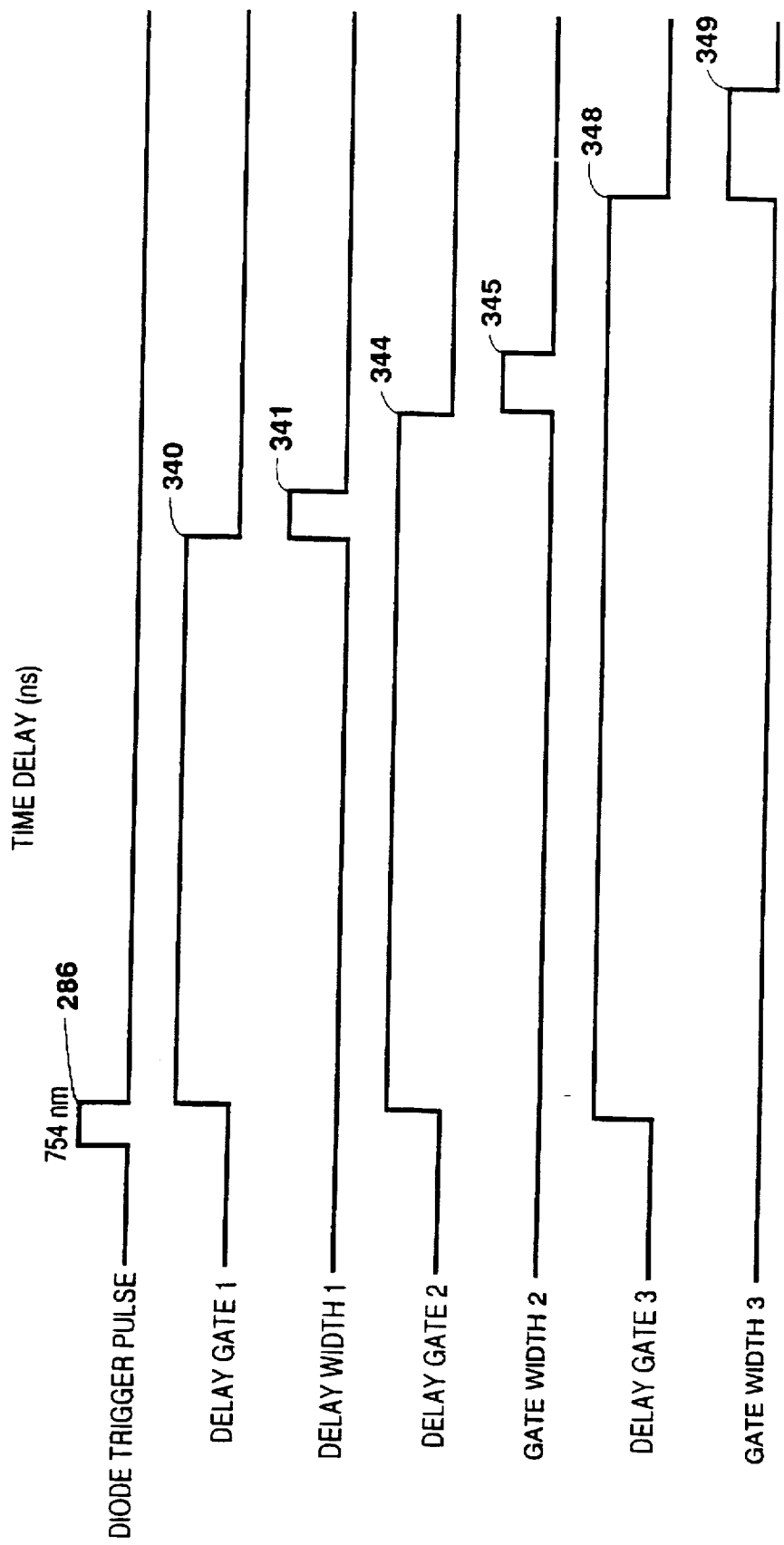

The gate arrangement of FIGS. 3A and 3B uses gates 341 and 345 to detect the decay slope of the signal while the third gate 349 may be used to determine the background signal. Outputs 342 and 346 of integrators 330 and 332 are used to calculate the slope.

To obtain approximately equal signal-to-noise ratios in the individual integrators, the length of the time windows is tailored to an exponential decay of the signal intensity with a logarithmic increase in the gate width with delay time.

Referring to FIGS. 3A and 3B, by scanning the delay gates (340, 344, and 348) and appropriately adjusting the gate widths, the system collects data corresponding to the entire detected pulse; subsequently, the shape (349) of the detected pulse is then calculated, i.e., time dependent light intensity profile I(t) is determined. The detected pulse shape, I(t), possesses information about the scattering and absorption properties of the examined tissue, which are closely related to the distribution of photon pathlengths in the tissue. The optical field is a function of the input-output port separation (ρ) as well as the optical properties of the tissue (absorption coefficient, $\mu_a$, scattering coefficient, $\mu_s$, and the mean cosine of anisotropic scattering, g). The general diffusion equation is used to describe the photon migration in tissue, as described by E. M. Sevick, B. Chance, J. Leigh, S. Nioka, and M. Maris in Analytical Biochemistry 195, 330 (1991) which is incorporated by reference as if fully set forth herein.

The system utilizes a previously determined solution for the fluence distribution in an infinite media as a Green's function with near infinite boundary conditions, wherein the diffusion equation is solved for the intensity of detected light in the reflectance geometry, $R(\rho,t)$, or the transmittance geometry $T(\rho,d,t)$. In the reflectance arrangement in a semi-infinite media with the separation of the input and output ports on the order of centimeters the reflectance was determined as follows:

$$\frac{d}{dt} \log_e R(\rho, t) = \frac{-5}{2t} - \mu_a c + \frac{\rho^2}{4Dct} \quad (10)$$

For $t \to \infty$ the absorption coefficient $\mu_a$ is determined as follows:

$$\lim_{t \to \infty} \frac{d}{dt} \log_e R(\rho, t) = -\mu_a c \quad (11)$$

wherein $\rho$ is the separation between input and detection ports and c is speed of light in the medium.

In cases where the approximation of infinite time is not valid, Eq. 10 can be rewritten to obtain $\mu_a$ as follows:

$$\mu_a c = -\frac{d}{dt} \log_e R(\rho, t) + \frac{\rho^2}{4Dct} - \frac{5}{2t} \quad (12)$$

The value for D can either be an average value for tissue or a value specific to tissue type being measured such as head or breast.

The effective scattering coefficient (1-g) $\mu_s$ is determined as follows:

$$(1-g)\mu_s = \frac{1}{\rho^2} (4\mu_a c^2 t_{max}^2 + 10ct_{max}) - \mu_a \quad (13)$$

wherein $t_{max}$ is the delay time at which the detected reflectance time profile $(R(\rho,t) \equiv I(t))$ reaches maximum. The right hand side of Eq. 3 is the decay slope of the arrival time of the modified pulses.

The systems of FIGS. 2 and 3 enable direct, real-time output of the absorption coefficient $\mu_a$, tissue saturation (Y), average optical pathlength (<L>), and the scattering coefficient $\mu_s$. The absorption coefficient is quantified by evaluating the decaying slope of the detected pulse, as described in Eq. 11. The effective scattering coefficient, $(1-g) \cdot \mu_s$, is determined from Eq. 13.

Figure 3C:
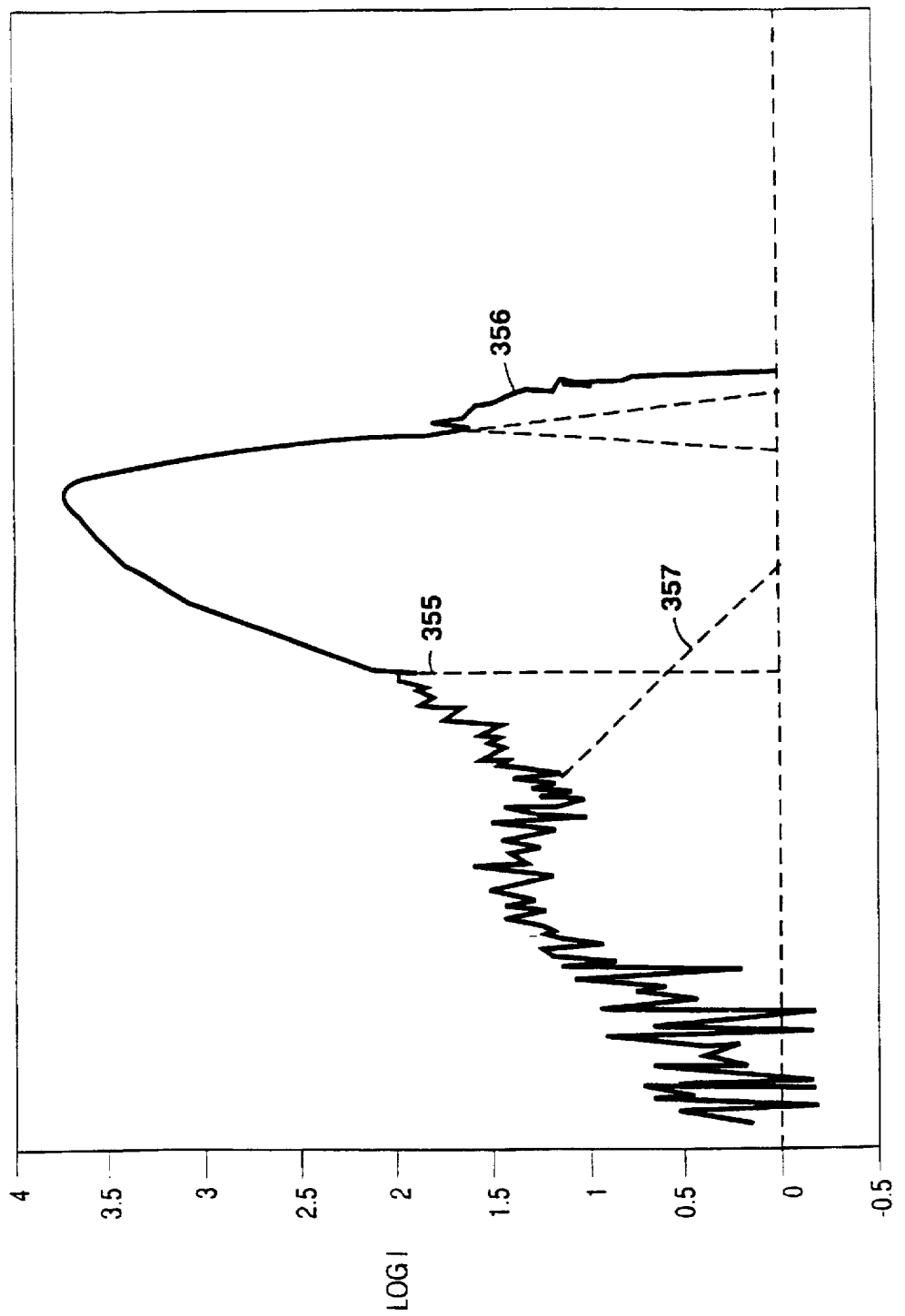
FIG. 3C shows a time resolved spectrum of photons that migrated through tissue with regions of different absorption and scattering properties.

As stated above, the intensity profile of the detected pulse, I(t), is strongly dependent on the absorption and scattering properties of the examined tissue. For a relatively homogeneous tissue (e.g., breast tissue), the detected pulse, in general, exhibits a single exponential decay (FIG. 3B). In cases wherein the light pulse migrates through different types of tissues (e.g., brain tissue that includes the white matter and the gray matter), the detected profile (I(t)) includes "two or more superimposed pulses", each characteristic of one type of tissue (Note pulse shapes 355, 356, and 357 in FIG. 3C). The TRS system of FIGS. 1, 2 or 3 scans the delay gates over the entire arrival time delay of the migrating photons to collect and deconvolute the intensity profile, I(t). A computer processor then fits iteratively the intensity profile to two or more overlapping curves and determines the scattering and absorption coefficients for each tissue effectively using Eqs. (10) and (13).

Photons introduced at the detection port are scattered on their migration path that depends on the number of scattering events. In highly scattering tissue, the time-of-flight of photons is the longest and photons have the greatest probability of penetrating larger volumes of tissue. The time-of-flight (or mean time <t>) is proportional to the pathlengths travelled by the photons, assuming that they travel at a speed c/n (wherein c is the speed of light in vacuum and n≈1.36 is the average refractive index of tissue). From the detected and deconvoluted photon intensity profile, I(t), a mean pathlength of the distribution of pathlengths is determined as follows:

$$<L> = \frac{c}{n} \frac{\int_0^\infty I(t)t\partial t}{\int_0^\infty I(t)\partial t} \quad (14)$$

Photon migration theory predicts that the detected photons can be represented by a three dimensional "banana-shaped" distribution pattern in the reflection geometry or a "cigar-shaped" distribution pattern in the transmission geometry. The concavity or shallow boundary is due to the escape of photons that reach the air-scatterer interface while the deeper boundary is due to attenuation of long path photons by the absorbers. If the tissue absorption properties are nonuniform, for example, when an absorbing object such as bleeding or a tumor is present, then the distribution of pathlength is also nonuniform.

The optical field is moved through tissue by increasing $\rho$ to achieve deeper field penetration or by moving the input port and the detection port in a scanning motion.

When the absorbing object is infinitely far away from the field, it does not alter the banana-shaped optical field. As the optical field is moved closer to the strongly absorbing object, the photons which have migrated the farthest distance from the input and detection ports are eliminated by the absorption process inside the absorber. Since photons with the longest pathlengths are absorbed, the approach of the field to the absorbing object shortens the distribution of pathlengths, detected as reduction in the average pathlength <L>. As the optical field moves even closer to the absorbing object, some of the detected photons can migrate around the object without being absorbed; this is detected as lengthening of the distribution of pathlengths. Thus, the average pathlength measurement reveals location of a strongly absorbing component of a tissue (e.g., tumor or localized bleeding); this is one way how the tissue absorbing component can be imaged.

Alternately, localization of an absorbing (or transparent) tissue component can be performed by moving the input port and the detection port on the subject and then creating two dimensional maps of the average photon migration pathlength <L>, the absorption coefficients, the scattering coefficients, measured values of different solutes, etc.

Figure 4:
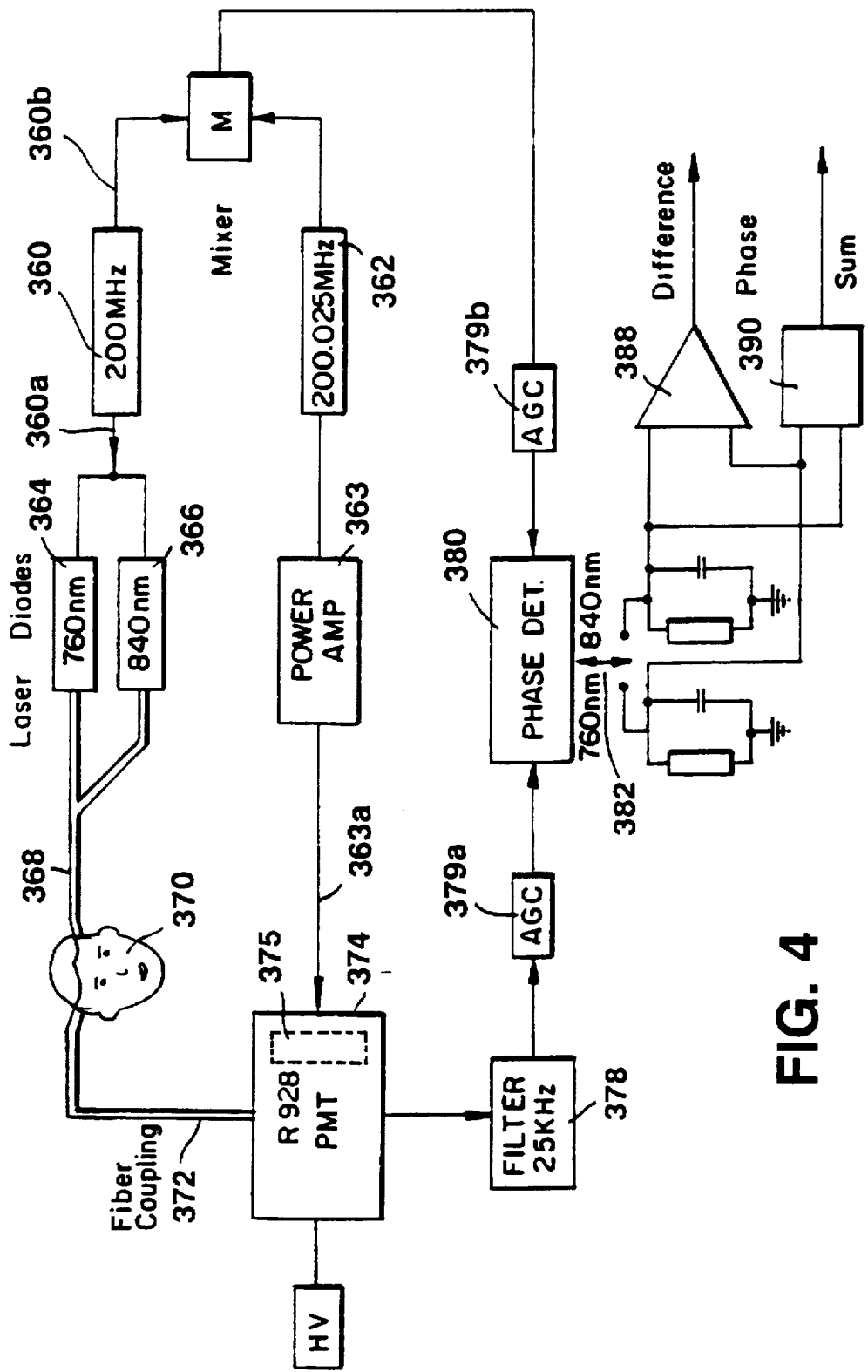
FIG. 4 is a block diagram of a dual wavelength PMS system in accordance with the present invention.

Another preferred embodiment of the optical probe is described in the U.S. Pat. 5,187,672, which is incorporated by reference as if fully set forth herein. The optical probe is a PMS system is shown in FIG. 4. The probe includes master oscillator 360 operating at 200 MHz and master oscillator 362 operating at 200.025 MHz. Oscillator 360 directly drives two laser diodes 364, 366, which emit 760 nm and 840 nm light (or 754 nm and 816 nm light). The light source is time shared by small mirror excited by a 60 Hz chopper. The fiber optic coupler 368 between the laser diodes 364, 366 and the subject is nominally 3 mm; two 8 mm couplers 372 collect photons for the R928 PMT detector 374. The second dynode (not shown) of PMT 374 is modulated with a 200.025 MHz reference signal generated by amplifier 363; thus the PMT experimental signal will have a frequency of 25 KHz. The PMT 374 alternately detects the 760 nm and 840 nm light (or 754 nm and 816 nm light) and produces corresponding output signals which are filtered by a filter 378 and leveled by the AGC circuit 379. A phase detector 30 generates a signal indicative of the phase of each output signal relative to the phase of a 25 MHz reference signal. The reference signal is produced by mixing the 200 and 200.025 MHz oscillator signals. The outputs of phase detector 30 are alternately selected by electronic switch 382, filtered, and then input to adder 390 and a subtracter 388 to produce sum and difference signals proportional to $<L>_{760}+<L>_{840}$ and $<L>_{760}-<L>_{840}$. The sum and difference signals are then used to calculate hemoglobin deoxygenation and blood volume.

Figure 4A:
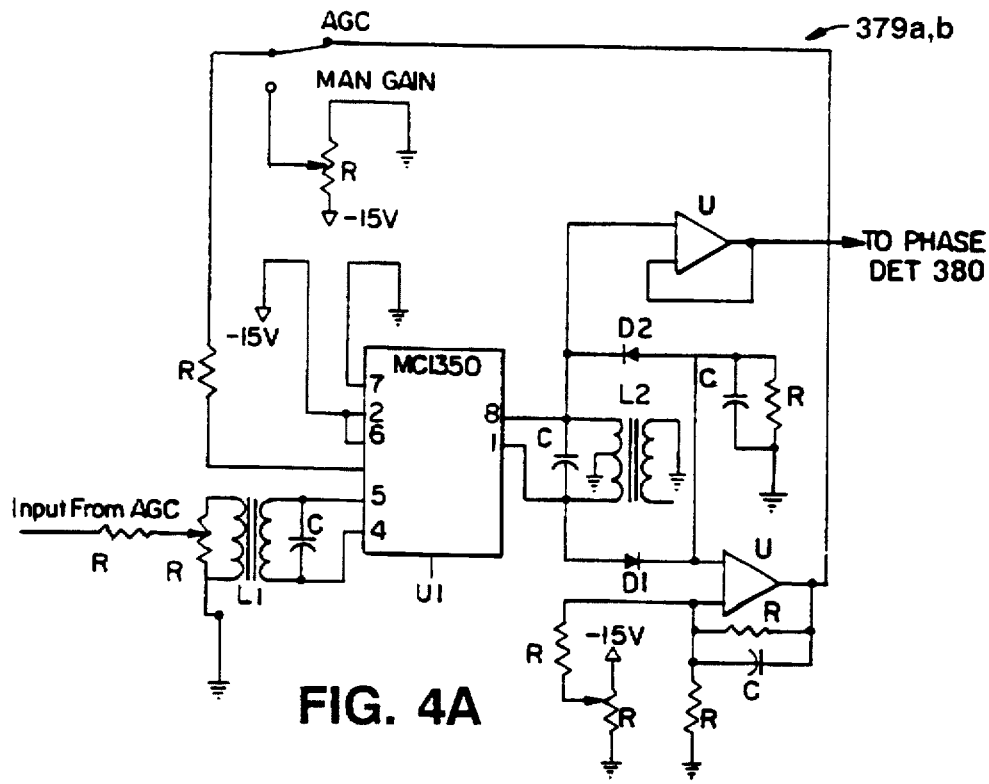
FIG. 4A is a schematic diagram of oscillator circuit 10 of FIG. .

A schematic diagram of a preferred oscillator 360, 362 as shown in FIG. 4A. The crystal is neutralized which makes it possible to operate it at resonance, where long-term stability can be expected. The respective crystals of oscillators 360 and 362 are offset from each other by 25 KHz. This circuit provides sufficient output power to directly drive a 5 mW laser diode.

Figure 4B:
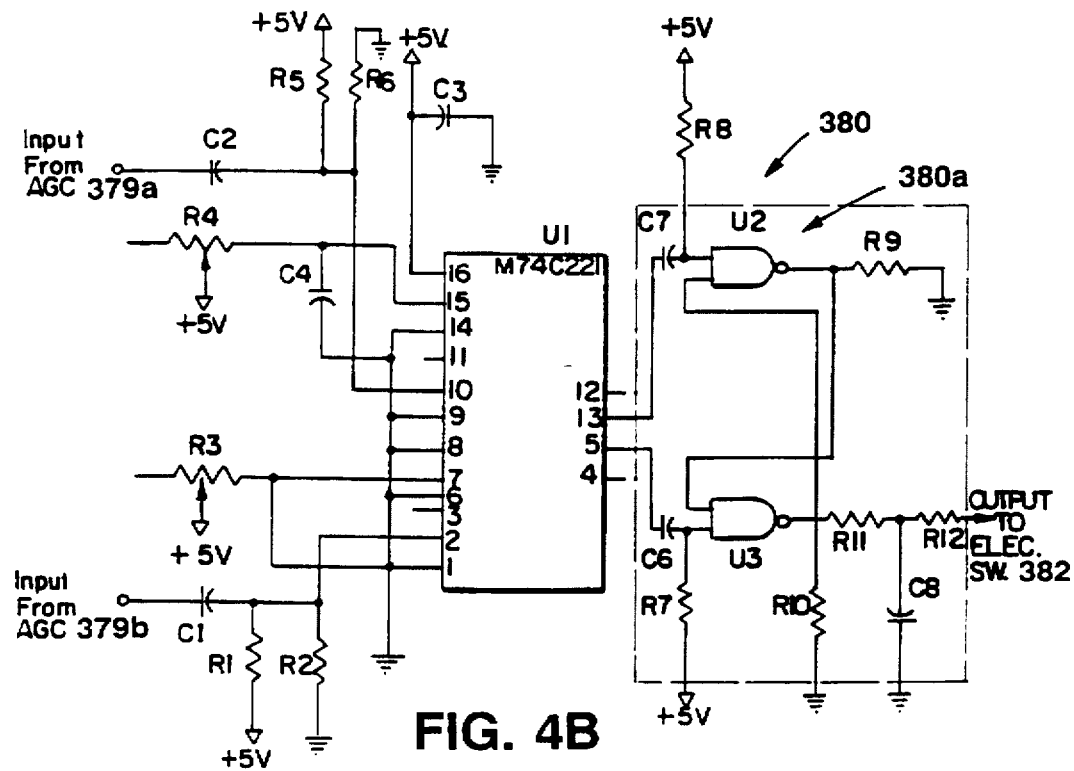
FIG. 4B is a schematic diagram of a PMT heterodyne modulation and mixing network in accordance with the present invention.

Another circuit, shown in FIG. 4B, which presents a significant improvement over previously-used circuits is the modulation circuit 375 for dynode number 2 of the PMT 374. This circuit uses a resonant circuit 375a with an impedance of 20,000 ohms instead of the usual 50 ohm load with very high power dissipation, providing a 50 volt drive of the photomultiplier dynode while dissipating only a few watts of power.

Figure 4C:
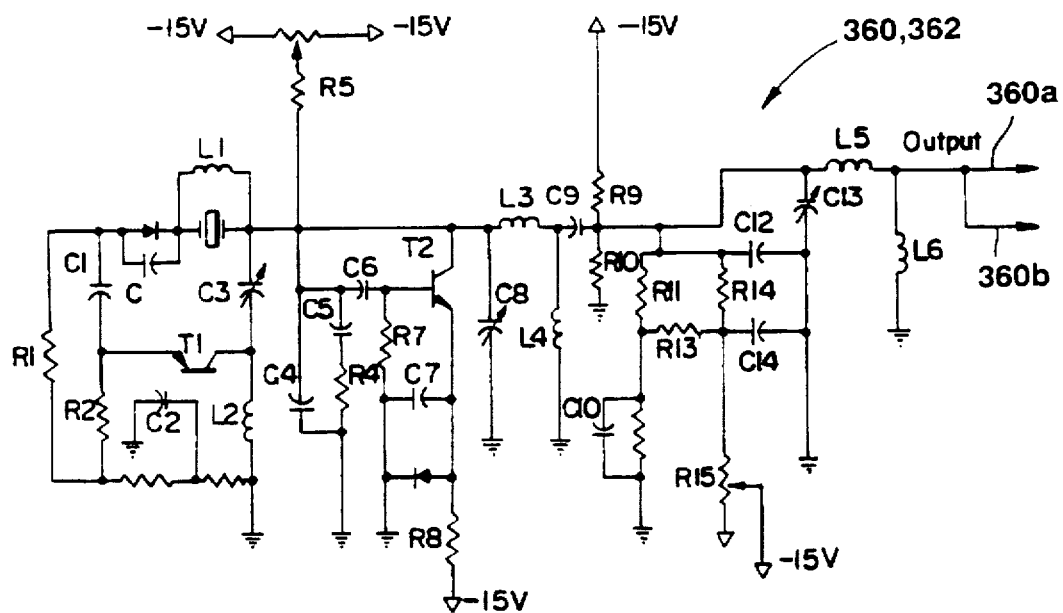
FIG. 4C is a schematic diagram of an AGC circuit in accordance with the present invention.
Figure 4D:
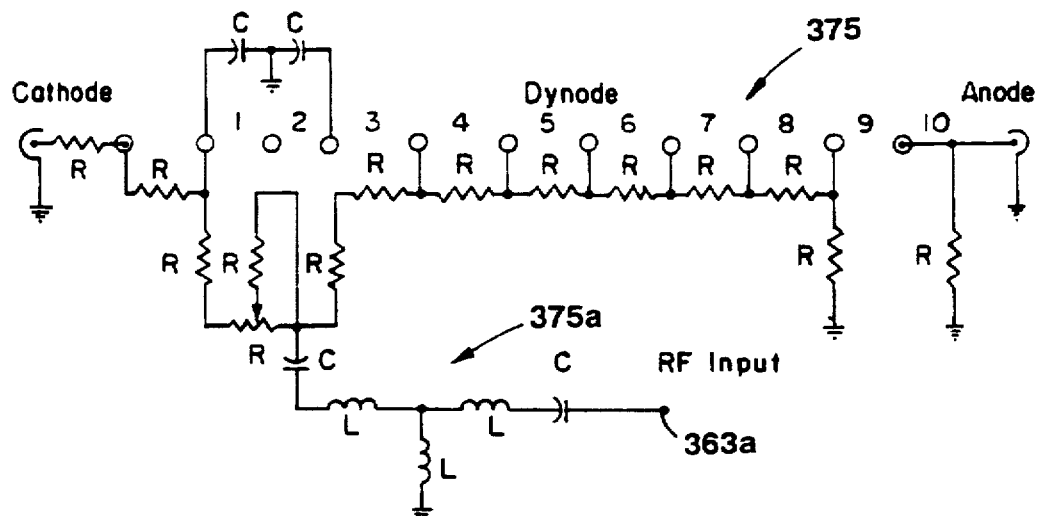
FIG. 4D is a schematic diagram of a phase detector circuit in accordance with the present invention.

To obtain stable operation of the phase detector, a stable input signal is required. The 25 KHz AGC circuit 375 illustrated in FIG. 4C includes an MC 1350 integrated circuit U1, featuring wide range AGC for use as an amplifier. The signal amplitude is controlled by a feedback network, as shown. A major reason why phase changes are accurately detected by the PMS system in accordance with this embodiment of the present invention is that the phase detector input signal level is nearly constant due to the AGC circuit.

Healthy vertebrate cells commonly maintain a lower concentration of $Na^+$, and a higher concentration of $K^+$, than is found in the surrounding extracellular fluid or blood plasma. $Na^+$ transport is driven by light, oxidation, or ATP hydrolysis. An integral membrane protein, $Na^+$—$K^+$ ATPase, bears primary responsibility for establishing and maintaining this transmembrane electrochemical potential, by coupling export of $Na^+$ ions with import of $K^+$ ions in a three-to-two ratio respectively.

Transmembrane electrical and chemical gradients are essential to the health of a cell, particularly for signaling in neurons and contraction in muscle cells. Chemical ion gradients further provide the driving force for cotransport of solutes into the cell, by coupling the spontaneous downhill flow of $Na^+$ with simultaneous uphill pumping of other solutes. Examples of coupled solutes include other types of ions, such as $Ca^{++}$, dicarboxylic acids, amino acids, or sugars such as lactose, sucrose, glucose, and mannose. The solutes confined in the cell exert osmotic pressure on the plasma membrane. Thus, the $Na^+$—$K^+$ ATPase regulates cell volume by controlling intracellular solute concentrations, thereby causing the cell to swell or to shrink.

Because ion gradients are essential for active transport and energy conservation, collapse of ion gradients across cellular membranes can cause serious physiological pathologies. Accordingly, the various methods disclosed herein are useful for detecting and monitoring a physiological disorder involving ionic disequilibration of an electrochemical gradient. The methods of the invention can be applied to a variety of cell types and tissues, both non-neural and neural, including peripheral nerves, spinal cord nerves and brain cells such as cortical neurons. Examples of applicable disease states include, but are not limited to, disorders due to ischemia, including ischemic cerebrovascular disease due to, e.g., thrombosis, embolism, or stroke; ischemia of the colon; ischemia associated with encephalopathy; intestinal ischemia due to, e.g., a gastrointestinal ulcer; renal ischemia; ischemic disease of the vascular system, e.g., coronary artery disease or heart disease; physical trauma; excessive elevation of the extremities during, e.g., surgical operations; chemotherapeutic agents; poisons such as quinine or an environmental toxin; or exsanguination. "Ischemia", as used herein, refers to inadequate perfusion, which results in diminished oxygen or hypoxia.

The methods of the invention are further useful for disorders involving ionic disequilibration caused by, e.g., an ionophore, a chemical compound which facilitates transport of an ion down its concentration gradient, so as to deflate polarization of that gradient. Examples include ionophores such as antibiotics, e.g., valinomycin and monensin, and chemotherapeutics. Also embraced are peripheral neuropathies, including, but not limited to, alcoholic polyneuropathy and hypoglycemia.

The invention was tested using the PMS apparatus described above. The phase shift $\theta$ of emergent light relative to incident light can be measured with a system that emits light at wavelengths sensitive to hemoglobin deoxygenation (e.g., 754–760 nm) and oxygenation (e.g. 816–840 nm); therefore changes in hemoglobin oxygenation alter the distribution of the photon paths and shift the measured phase $\theta$ is reported in terms of $<L>$, the effective pathlength, by using the relations $\theta=2\pi f<L>/nc$, where c is the speed of light ($3*10^{10}$ cm/s), n is the refractive index of the medium (1.33 for an aqueous solution), and f is the modulation frequency (220 MHz), as described by E. M. Sevick, B. Chance, J. Leigh, S. Nioka, and M. Maris in Analytical Biochemistry 195, 330 (1991) incorporated by reference. Changes in $<L>$ can be used to monitor changes in hemoglobin oxygenation and total hemoglobin concentration when measured at a wavelength that straddles the isosbestic point of hemoglobin (800 nm), e.g., at $\lambda=754$ nm and 816 nm. Thus hemoglobin saturation may be effectively monitored from the measured changes in $<L>$.

In the study, a dual wavelength PMS system was used to measure $<L>$ during changes in blood flow (ischemia), tissue oxygen concentration (hypoxia) and ionic hemeostasis (spreading depression) in rodent brains. In addition, measurements of $<L>$ were compared to measurements of tissue metabolism, electrical activity and blood flow. The changes in hemoglobin monitored by using light at 754 and 816 nm were found to correlate with intracellular events such as the reduction of AND+ and the loss of electrical activity. See Mahevsky, Sclarsky, "Correlation of Brain NADH Redox State, K+, $PO_2$ and Electrical Activity During Hypoxia, Ischemia and Spreading Depression." Oxygen Transport to Tissue-IV, 129–141 (1983).

A rodent brain was chosen as the experimental model for two major reasons: it is a well characterized model, and the brain blood supply, oxygenation and ionic homeostasis can be easily manipulated. In addition, the carotid arteries can be readily isolated and occluded to induce ischemia and respiratory gases can be controlled to induce hypoxia.

Spreading depression (SD) is a unique brain phenomenon that is thought to be associated with migraine headaches. It is initiated by a localized infarct that results in depolarization of the neural and glial cell membranes of the outer cortex of the brain. The depolarization is characterized by a release of K+ from cells of the cortex and a shift of extracellular Na and Ca into the cells. The depolarization wave spreads from the infarct at a velocity of 3 mm/min and results in vasoconstriction and hypoperfusion in the outer cortex, followed by vasodilation and greatly increased metabolic activity during polarization recovery. It has been found, however, that there is depressed blood flow by 20–25% for at least an hour after the SD. It has also been found that the extracellular space decreases during depolarization by as much as 50%. Since the vascular, metabolic and physical changes are unique during SD, the effects of SD on <L> are quite different from the effects of hypoxia or ischemia on <L>; thus changes in $<L>_{754}$ and $<L>_{816}$ are used to monitor the physiological response of the brain to SD.

In this study, <L> was compared to independent measurements of brain function to determine its utility as a brain monitoring parameter. During hypoxia and ischemia, deoxygenation is accompanied by a decrease in $<L>_{754}$ and an increase in $<L>_{816}$; reoxygenation is accompanied by an increase of $<L>_{754}$ and an increase in $<L>_{816}$. As total tissue blood volume increases, pathlengths at both wavelengths decrease, and as total tissue blood volume decreases, pathlengths increase. In the study, independent measurements of pathophysiology consisted of brain metabolism (NADH fluorescence), electrical activity (ECoG), and blood flow (doppler flow).

Briefly, the system used in the study included two laser diodes emitting radiation at wavelengths of 754 nm and 816 nm, although other wavelengths could have used. The laser diodes were sinusoidally modulated at 220.010 MHz and 220.025 MHz. Light was brought to the rodents' brains from each laser diode with a bifurcated plastic optical fiber having a 1 mm diameter. Light transmitted through the subject was received by a 1 mm glass optical fiber and detected by a Hamamatsu R928 photomultiplier (PMT). Heterodyne mixing of a third 220 MHz oscillator signal with the 220.010 MHz and 220.025 MHz signals produced 10 KHz and 25 KHz reference signals. The 220 MHz signal was also coupled to the second dynode of the PMT to facilitate dynode mixing and generation of 10 KHz and 25 KHz experimental signals. The experimental signals were compared to the reference signals in a phase detector. The two output voltages from the phase detector represented the respective phase differences between the 754 nm and 816 nm experimental signals and the reference signal.

To calibrate the system, a voltage proportional to the phase shift of the emergent light relative to the incident light was recorded. To correlate the voltage to the change in phase, voltage measurements were recorded for various concentrations (µs) of a known scatterer. The known scatterer was a fat emulsion (Intralipid 20%) diluted to about the physiological scattering range (1%) to achieve a scattering concentration of 14.5 cm$^{-1}$ with negligible absorption. From the separations ρ, concentrations µs and measured phase shifts θ, <L> can be calculated using the photon diffusion approximation. See Sevick, et al., "Non-invasive and Dynamic Measurement of Hemoglobin Saturation in Perfused Tumors." J. Cancer Research and Clinical Oncology, 116, S514 (1990). The slope (calculated using linear regression from the voltage and <L> values measured during calibration) was used to calculate <L> from voltages recorded during the experimental studies.

Each animal was anesthetized by intraperitoneal injection of Equi-Thesin (0.3 ml/100 g body weight). Each skull was surgically exposed and a 5 mm hole was made in the right parietal bone. The dura matter of the brain surface was carefully removed from the area where the K+ electrode was placed. A multiprobe assembly (MPA) (described below) was then placed above the cortex without putting pressure on the brain. four steel screws were placed in the skull to provide an anchor. Ground and reference electrodes were placed below the skin and were cemented to the skull together with the MPA and the screws. The left and right carotid arteries were surgically exposed and sutures were placed around them to initiate ischemia. Nitrogen was used to initiate hypoxia. A topical application 0.5M, 1.0M of aqueous KCL was used to initiate SD. All probes were held in place by a Delrin canula, except the PMS detecting fiber which was placed 8 mm posterior and on the same hemisphere as the MPA. The MPA consisted of a delrin canula that held light guides for NADH fluorescence, doppler flow, and PMS light inputs.

The intramitochondrial NADH redox state was monitored with a light guide fluorometer/reflectometer. The source for the 366 nm light was a 100-watt mercury arc cooled by air. The emitted light was split in a 90:10 ratio for measurement of the NADH fluorescence and reflectance, respectively. The light entered the tissue and was either reflected out of the tissue or absorbed by NADH, which then fluoresced at 435 nm. The ratio of the fluoresced and reflected light compensated for any blood volume changes in the tissue and provided a measurement of intramitochondrial NADH levels. The common part of the bifurcated light guide was cemented inside the MPA.

The doppler blood flow meter was a commercial model (manufactured by Transonics Inc., Ithaca, N.Y.) that emitted light at 633 nm. The doppler flow meter NIR light affected the FRS measurements by contributing a large DC light background to the PMT. This made it necessary to operate the FRS and doppler flow meter independently of each other.

The ECoG monitored each brain's electrical activity by measuring the DC and electrical changes of the outer surface of the brain cortex. A Ag/Cl wire was used to measure the DC potential while a series of stainless steel wires placed concentrically around the Ag/Cl were used to measure electrical activity. For detailed description see A. Mayevsky, et al., "A fiberoptic Based Multiprobe System For Intraoperative Monitoring of Brain Functions" SPIE Vol. 1431, 1991.

Hypoxia, caused by 100% $N_2$ inspiration, caused a decrease in $<L>_{754}$ of 1 to 3 mm and an increase in $<L>_{816}$ of 1 to 2 mm. If the hypoxic/ischemic episode lasted for greater than 40 seconds, there was an overshoot in $<L>_{754}$ of about 1 mm that took 3–5 minutes to return to the baseline value. $<L>_{816}$ dropped by as much as 2 mm and took 2–5 minutes to recover to a baseline after restoration of $O_2$. The degree of change in <L> varied between animals and during hypoxic episodes in the same animals.

The effects of hypoxia on ECoG and NADH were detected within 20 seconds. The NADH signal changed maximally in 55 seconds as the intramitochondrial NAD$^-$ became fully reduced to NADH. The ECoG signal dropped to zero at the same time the NAD$^+$ became fully reduced. The blood flow showed a change in 20 seconds and reached maximal flow at 80 seconds.

The effect of ischemia on <L> was considerably less than the effect of hypoxia. The respective ranges of $<L>_{754}$ and $<L>_{816}$ prior to ischemia were 2.6–2.9 cm and 3.0–3.4 cm (the measurements were made with a source-detector separation of 8 mm). $<L>_{754}$ decreased by less than 1 mm and $<L>_{816}$ increased by about 1 mm during most ischemic episodes. During reflow of blood to the brain, $<L>_{754}$ returned to baseline; in contrast, $<L>_{816}$ often decreased below the baseline by a fraction of a mm.

Ischemia did not change the NAD signal until 20 seconds after the occlusion of the carotid arteries. Intracellular $O_2$ became completely depleted after this critical period, whereupon the NAD signal started to rapidly change as the NAD was reduced to NADH. After 40 seconds of bilateral ischemia the NAD was completely reduced to NADH. The rodent brain generally showed depressed electrical activity after changes in the NADH and $<L>$ were observed. The ECoG became depressed in 30 seconds and all electrical activity ceased in 45 seconds. The blood flow generally dropped to a minimal value after 20 seconds of bilateral occlusion. Reflow resulted in a transient increase in blood flow to the brain.

The depolarization phase of the SD wave caused a parallel increase of $<L>_{754}$ and $<L>_{816}$. The peak increase of $<L>$ for both wavelengths took 40–160 seconds and was about +2 mm. There was generally an undershoot in $<L>$ of about 2 mm that took 80–180 seconds. $<L>$ recovered to baseline after 240 seconds; however, the animal often experienced a series of SD waves that resulted in periods of increasing and decreasing $<L>$.

The goal of the study was to determine whether the changes in photon pathlengths at 754 at 816 mm are correlated with changes in local flow, electrical activity, and intracellular NADH levels within the cortex of a rodent brain insulted by hypoxia, ischemia, and SD. The results show that the changes in photon pathlengths during hypoxic and ischemic insults are indicative of deoxygenation of hemoglobin in the vascular space. It has also been found that the pathlength changes: (i) are correlated to changes in NADH levels (using ANOVA statistical tests), and (ii) precede the measured changes in intracellular NADH content and transmembrane potentials. In other words, deoxygenation of the vascular space preceded the intracellular response. The later finding confirms the important link between oxygen availability, metabolic energy, and the electrical potential gradient maintained by the $Na^+$ $K^+$ AtPase transmembrane pump. More importantly, these results indicate that PMS can accurately detect alteration in tissue oxygenation before actual insult to intracellular metabolic assemblies occur.

The results also show that changes in photon pathlengths caused by the wave of depolarization during SD are markedly different from changes caused by ischemic and hypoxic episodes. It has been observed that increases of photon pathlengths measured at both wavelengths as well as increased levels of NADH immediately following the depolarization wave as monitored with ECoG. This suggests SD causes either a decrease in total blood volume caused by vasoconstriction or an increase in the scattering properties of the cortex. Regardless, the results illustrate the ability of dual-wavelength PMS to discern pathophysiologic changes whether they entail changes in vascular volume or alteration in extracellular space.

Figures 5A, 5B:
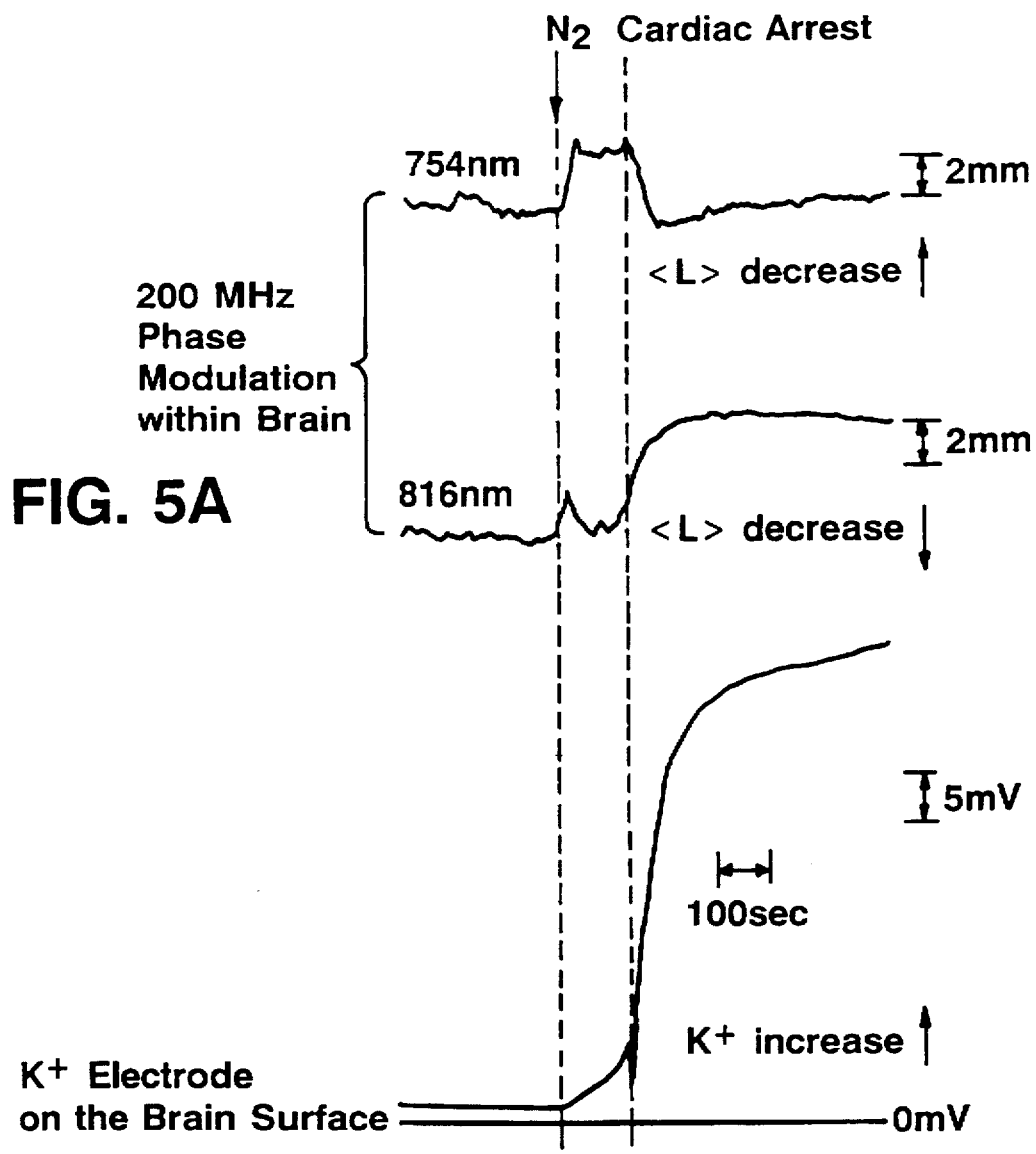
FIG. 5A represents a plot of the phase shifts measured for the 754 nm and 816 nm wavelengths during hypoxia and cardiac arrest.
FIG. 5B represents a plot of a potassium level measured by a surface electrode on the brain during hypoxia and cardiac arrest.

Referring to FIGS. 5A and 5B, in another study, osmotic changes were imposed upon the rat brain to measure changes in the scattering and absorption properties of the cortical neurons. (Similar measurements could have been performed other types of human tissue listed above to measure neural activity of the tissue.) The skull of the rat was partially opened to position a $K^+$ surface electrode on the surface of the brain, as described above. The optical input and detection ports were placed externally on the rat head for transcranial examination. The osmotic changes were imposed by tail vein injection of relatively high concentrations of sucrose, i.e., 100 µl of 200 mM sucrose in a 300 gm rat. Using the above described PMS method, light scattering changes were observed within the next 30 seconds. As shown in FIG. 5A, initially the tissue scattering increased which causes an increase in the phase shift at both 754 nm and 816 nm wavelengths. The scattering increases are attributed to the movement of mannitol through the BBB into the extracellular space of the brain. However, the changes are transient, which suggest that such osmotic effects are minimized by uptake of the osmolyte into the cortical tissue volume.

The scattering increases correspond to the potassium release from the intracellular to the extracellular space of the brain; this is confirmed by the increase in potassium on the surface measured by the potassium electrode, as shown in FIG. 5B. FIGS. 5A and 5B provide a good correlation of the potassium release between the two types of measurement. However, the optical changes are transient, which suggest that the osmotic effects are minimized by uptake of the osmolyte into the cortical tissue volume. As pointed out above, the 754 nm light is sensitive to deoxyhemoglobin. Thus, during the cardiac arrest absorption of the 754 nm light increases which causes decrease in the measured $<L>_{754}$.

The scattering properties of the examined tissue change due to the change of the refractive index, where the critical parameters are the cell diameter, $N_e$ (refractive index of the extracellular space), and $N_i$ (refractive index of the intracellular space). The refractive index change is caused by the release of potassium and the uptake of water in the cortical neurons during the described hypoxia and ischemia. It should be pointed out that the cell diameter contains not only the cell volume but also the volume of cellular organelles, particularly mitochondria, expected to be swelled under hypoxia-ischemia ionic disequilibration.

In another embodiment, the optical probe includes a continuous wave (CW) system described in the WO 96/16592 document, published on Jun. 6, 1996, incorporated by reference as if fully set forth in its entirety herein. The CW system, also described in WO 92/20273, introduces continuous wave light of selected wavelengths in the examined tissue and detects light scattered and absorbed while migrating over the migration paths. A processor receives data corresponding to the detected light and determines changes in the scattering or absorptive properties of the tissue, as described in the WO 96/16592 document. The scattering or absorptive properties depend on the levels of electrolytes in the intracellular and extracellular space of the examined tissue.

The above described invention may be used for monitoring of the neural activity or for early detection of acute stages of hyperkalemia. Once the hyperkalemia is detected, different maneuvers can be used for rapid treatment. Intravenous injection of glucose plus insulin, or sodium bicarbonate, may be used to promote the transfer of $K^+$ from the extracellular fluid to the intracellular fluid. Potassium elimination from the body may be stimulated by diuretics, exchange resins, and dialysis. Finally calcium can be administered to urgently counteract the effects of hyperkalemia on cardiac excitability.

Further embodiments are within the scope of the following claims:

I claim:

1. A spectroscopic method for non-invasive in vivo examination of neural activity comprising the steps:

introducing into biological tissue, at an irradiation location on the tissue, electromagnetic radiation of a visible or infra-red wavelength;

detecting photons of electromagnetic radiation of said wavelength that have migrated in the tissue over photon migration paths from said irradiation location to a detection location on the tissue spaced a given distance from the irradiation location;

evaluating photon scattering of the tissue corresponding to changes in the refractive index of the tissue attributable to release of potassium from cells of the tissue leased on said detecting step; and determining neural activity of the tissue based on said evaluation of photon scattering of the tissue.

2. The method of claim 1 further comprising the steps of introducing into the tissue, at said irradiation location, electromagnetic radiation of a second visible or infra-red wavelength;

detecting photons of electromagnetic radiation of said second wavelength that have migrated in the tissue from said irradiation location to said detection location; and said determining step further includes evaluating photon scattering of the tissue corresponding to changes in the refractive index of the tissue at said second wavelength.

3. The method of claim 2 further including the steps of detecting photons of said wavelength that have migrated in the tissue over photon migration paths between said irradiation and detection locations that are spaced apart a different distance than said given distance; and performing said evaluating step based on said detected photons that have migrated over said different distance.

4. A method for non-invasive in vivo examination of neural activity by spectroscopic examination of tissue comprising the steps of generating a carrier waveform at a frequency on the order of magnitude of $10^8$ Hz, said frequency having a time characteristic compatible with the time delay of photon migration from an irradiation location to a detection location on the examined tissue, and imposing said generated carrier waveform upon electromagnetic radiation of a visible or infra-red wavelength to obtain modulated radiation;

introducing into biological tissue said modulated radiation at said irradiation location;

detecting over time photons of said introduced radiation of said wavelength that have migrated in the tissue over photon migration paths from said irradiation location to said detection location;

determining a phase shift between said introduced radiation and said detected radiation; and evaluating, based on said phase shift, photon scattering corresponding to changes in the refractive index attributable to release of potassium from cells of the tissue and determining therefrom neural activity of the examined tissue.

5. The method of claim 4 wherein said step of evaluating photon scattering includes calculating the scattering coefficient of the examined tissue based on said phase shift.

6. The method of claim 4 wherein said step of evaluating photon scattering includes calculating an effective pathlength of photon migration in the tissue based on said phase shift.

7. The method of claim 4 further comprising the steps of imposing said generated carrier waveform upon electromagnetic radiation of a second visible or infra-red wavelength to obtain second modulated radiation;

introducing into biological tissue said second modulated radiation at said irradiation location;

detecting over time photons of said second wavelength that have migrated in the tissue over photon migration paths from said irradiation location to said detection location;

determining a second phase shift between said introduced radiation and said detected radiation of said second wavelength; and evaluating photon scattering based on said second phase shift.

8. The method of claim 4 or 7 wherein said wavelengths are selected to reduce absorption variation due to changes in hemoglobin oxygenation or blood volume.

9. The method of claim 2 further comprising the steps of generating a second carrier waveform at a second frequency on the order of magnitude of $10^8$ Hz;

imposing said second carrier waveform upon electromagnetic radiation of said wavelength to obtain second modulated radiation;

introducing into biological tissue said second modulated radiation of said second frequency at said irradiation location;

detecting over time photons of said second modulated radiation that have migrated in the tissue over photon migration paths from said irradiation location to said detection location;

determining a second phase shift between said introduced radiation and said detected radiation that had been modulated by said second frequency; and evaluating photon scattering based on said second phase shift.

10. The method of claim 7 or 9 wherein said evaluating step includes determining the scattering coefficient of the examined tissue based on said first and second phase shifts.

11. A spectroscopic method for non-invasive in vivo examination of neural activity comprising the steps of generating pulses having an input waveform of duration on the order of a nanosecond or less;

imposing said generated pulses of said input waveform upon electromagnetic radiation of a visible or infra-red wavelength to produce pulsed radiation;

introducing into biological tissue said pulsed radiation at an irradiation location on the tissue;

detecting over time photons of said introduced radiation of said wavelength that have migrated in the tissue from said irradiation location to a detection location on the tissue;

storing over time signals corresponding to said detected photons that represent a detected pulse waveform at said wavelength;

evaluating photon scattering of the tissue based on change in the shape of the detected pulse waveform and the input pulse waveform, at said wavelength said photon scattering corresponding to changes in the refractive index attributable to release of potassium from cells of the tissue; and determining neural activity of the examined tissue based on said evaluation of photon scattering.

12. The method of claim 11 wherein said evaluating step includes calculating a scattering coefficient of the tissue.

13. The method of claim 1, 4 or 11 wherein said release of potassium from cells of the examined tissue occurs prior to permanent tissue damage.

14. The method of claim 1, 4 or 11 wherein said release of potassium occurs upon death.

15. The method of claim 1, 4 or 11 wherein said wavelength is selected so that absorption of said radiation does not depend on hemoglobin oxygenation.

16. The method of claim 15 wherein said wavelength is about 805 nm.

17. The method of claim 1, 4 or 11, after said determination of neural activity, further comprising the step of intravenously injecting a solute that reverses said release of potassium.

18. An optical probe for non-invasive in vivo monitoring of neural activity comprising a light source constructed to introduce electromagnetic radiation of a visible or infra-red wavelength into biological tissue at an irradiation location;

a detector constructed to detect photons of said radiation of said selected wavelength that have migrated in the biological tissue from said irradiation location to a detection location on the tissue; and a processor, receiving signals of said detected radiation, constructed and arranged to determine changes in photon scattering of the tissue corresponding to changes in the refractive index attributable to release of potassium from cells of the tissue and determine therefrom neural activity of the tissue.

19. An optical probe for non-invasive in vivo examination of neural activity comprising a first oscillator constructed to generate a first carrier waveform at a first frequency on the order of magnitude of $10^8$ Hz, said first frequency having a time characteristic compatible with the time delay of photon migration from an irradiation location to a detection location on the examined tissue;

a light source coupled to said first oscillator and constructed to generate electromagnetic radiation of visible or infra-red wavelength modulated by said first carrier waveform, said light source being constructed to introduce said modulated radiation into biological tissue at an irradiation location on the tissue;

a detector constructed to detect over time photons of said radiation of said wavelength that have migrated in the examined tissue from said irradiation location to said detection location;

a phase detector constructed to determine a phase shift between said detected radiation and said introduced radiation at said wavelength, said phase-shifted radiation being indicative of said scattering and absorptive properties of the examined tissue; and a processor, operatively connected to said phase detector, constructed and arranged to evaluate photon scattering corresponding to changes in the refractive index attributable to release of potassium from cells of the tissue based on the phase shift and determine therefrom neural activity of the examined tissue.

20. The optical probe of claim 19 further comprising a second oscillator constructed to generate a second waveform at a second frequency;

said detector arranged to receive a reference waveform at a reference frequency offset by a frequency on the order of $10^3$ Hz from said first frequency and to produce a signal, at said offset frequency, corresponding to said detected radiation; and said phase detector adapted to compare, at said offset frequency, the detected radiation with the introduced radiation and to determine therefrom the phase shift at said wavelength.

21. The optical probe of claim 16 or 17 wherein said processor is constructed and arranged to calculate the effective pathlength of photons of said wavelength migrating between said irradiation location and said detection location prior to determining the neural activity.

22. The optical probe of claim 19 or 20 wherein said processor is constructed and arranged to calculate the scattering coefficient at said wavelength of the examined tissue prior to determining the neural activity.

23. The optical probe of claim 19 wherein said first oscillator is constructed to generate a second carrier waveform at a second frequency on the order of magnitude of $10^8$ Hz, said second frequency having a time characteristic compatible with the time delay of photon migration from said irradiation location to said detection location on the examined tissue;

said light source is coupled to said first oscillator and constructed to generate said radiation modulated by said second carrier waveform;

said detector is constructed to detect over time photons of said radiation of said wavelength that have migrated in the examined tissue from said irradiation location to said detection location;

a phase detector is constructed to determine the phase shift between said detected radiation and said introduced radiation at said second frequency; and said processor is constructed and arranged to evaluate photon scattering also based on the phase shift at said second frequency.

24. The optical probe of claim 23 wherein said processor is constructed and arranged to calculate the scattering coefficient, at said second frequency, of the examined tissue prior to determining the neural activity.

25. The optical probe of claim 19 wherein said light source, operatively connected to said first oscillator, is constructed to generate electromagnetic radiation of a second selected wavelength modulated by said first carrier waveform; the optical probe further comprising a switch adapted to introduce interchangeably radiation at each said wavelengths into the tissue at said irradiation location; said detector being further adapted to detect, at said detection location, the radiation of said second wavelength that has migrated in said tissue between said irradiation and detection locations; said phase detector, operatively connected to said switch, being further adapted to compare, at said second wavelength, the detected radiation with the introduced radiation and to determine therefrom the phase shift of said detected radiation; and said processor further constructed and arranged to determine the neural activity based on the phase shift at said second wavelength.

26. The optical probe of claim 25 wherein said processor is constructed and arranged to calculate the effective pathlength of photons of said second wavelength migrating between said irradiation location and said detection location prior to determining the neural activity.

27. The optical probe of claim 25 wherein said processor is constructed and arranged to calculate the scattering coefficient at said second wavelength of the examined tissue prior to determining the neural activity.

28. An optical probe for non-invasive in vivo examination of neural activity comprising a light source constructed to generate pulses of radiation of a visible or infra-red wavelength and to introduce into biological tissue said pulsed radiation at an irradiation location, said pulses having an input waveform of duration on the order of a nanosecond or less;

a detector constructed to detect over time photons of said pulsed radiation of said wavelength that have migrated over photon migration paths in the tissue from said irradiation location to a detection location on the tissue;

an analyzer, connected to said detector and constructed to store over time signals corresponding to said detected photons that represent a detected pulse waveform at said wavelength; and a processor constructed and arranged to evaluate photon scattering corresponding to changes in the refractive index attributable to release of potassium from cells of the tissue based on change in the shape of the detected pulse waveform and the input pulse waveform and determine therefrom neural activity of the examined tissue.

29. The optical probe of claim 28 wherein said processor is constructed and arranged to calculate the effective pathlength of photons of said wavelength migrating between said irradiation location and said detection location prior to determining the neural activity.

30. The optical probe of claim 28 wherein said processor is constructed and arranged to calculate the scattering coefficient at said wavelength of the examined tissue prior to determining the neural activity.

31. The optical probe of claim 28 wherein said light source is further adapted to introduce into the tissue, at said input port, said pulses of electromagnetic radiation of a second selected wavelength in the visible or infra-red range;

said detector further adapted to detect, at said detection port, photons of modified pulses of said second wavelength that have migrated in the tissue from said input port;

said analyzer further adapted to determine a change in the pulse waveform shape of said detected pulses relative to said introduced pulses, at said second wavelength; and said processor further adapted to determine the neural activity based on said determined pulse waveform change at said second wavelength.

32. The optical probe of claim 31 wherein said processor is constructed and arranged to calculate the effective pathlength of photons of said second wavelength migrating between said input port and said detection port prior to determining the neural activity.

33. The optical probe of claim 31 wherein said processor is constructed and arranged to calculate the scattering coefficient at said second wavelength of the examined tissue prior to determining the neural activity.

34. The optical probe of claim 23, 25 or 31 wherein said wavelengths are selected to reduce absorption variation due to changes in hemoglobin oxygenation or blood volume.

35. The optical probe of claim 18, 19 or 28 wherein said processor is constructed and arranged to determine the neural activity prior to permanent tissue damage.

36. The optical probe of claim 18, 19 or 28 wherein said processor is constructed and arranged to determine the neural activity that occurs upon death.

37. The optical probe of claim 18, 19 or 28 wherein said wavelength is selected so that absorption of said radiation does not depend on hemoglobin oxygenation.

38. The optical probe of claim 37 wherein said wavelength is about 805 nm.

* * * * *